(12) United States Patent
Macaulay et al.

(10) Patent No.: US 6,291,428 B1
(45) Date of Patent: Sep. 18, 2001

(54) PEPTIDES WHICH PROMOTE BONE-FORMING CELL ATTRACTION AND ADHESION

(75) Inventors: William B. Macaulay, Eastchester, NY (US); Elizabeth Merrifield, Cresskill; Adele Boskey, North Caldwell, both of NJ (US)

(73) Assignees: The Hospital for Special Surgery; The Rockfeller University, both of New York, NY (US)

( * ) Notice: Subject to any disclaimer, the term of this patent is extended or adjusted under 35 U.S.C. 154(b) by 0 days.

(21) Appl. No.: 09/467,423

(22) Filed: Dec. 20, 1999

(51) Int. Cl.⁷ .............................. A61K 37/02; C07K 7/00
(52) U.S. Cl. .................... 514/12; 514/2; 514/955; 514/960; 530/300; 530/311; 530/324; 424/422; 424/464; 424/468
(58) Field of Search .................................. 530/327, 329, 530/350, 395, 300; 930/290; 435/69.1, 69.7; 514/86, 12, 107, 89, 141, 167

(56) References Cited

U.S. PATENT DOCUMENTS

| 5,866,113 | 2/1999 | Hendriks et al. ............... 424/78.17 |
| 5,876,454 | 3/1999 | Nanci et al. ...................... 623/16 |

OTHER PUBLICATIONS

Butler, 1989, Connect. Tissue Res., 23:123–36.
Butler, 1991, J. Biol. Buccale, 19:83:89.
McKee et al., 1992, Anat. Rec., 234:479–92.
McKee et al., 1992, J. Bone Miner. Res., 8:485–96.

Primary Examiner—Karen Cochrane Carlson
Assistant Examiner—Patricia Robinson
(74) Attorney, Agent, or Firm—Klauber & Jackson

(57) ABSTRACT

Peptides are provided with the properties of enhancing the migration and adhesion of bone-forming cells to a substrate, useful for promoting bone mineralization and osseointegration in the healing of, for example, orthopedic surgical procedures.

4 Claims, 1 Drawing Sheet

MC3T3 Adhesion

\* p < 0.05
\*\* p < 0.01

MC3T3 Chemotaxis

\* p < 0.05

PEPTIDES WHICH PROMOTE BONE-FORMING CELL ATTRACTION AND ADHESION

FIELD OF THE INVENTION

The present invention relates to peptides capable of promoting the attraction and adhesion of bone-forming cells, to promote bone ingrowth, osseointegration, and healing in surgical procedures involving bone and bone implants, including teeth.

BACKGROUND OF THE INVENTION

The use of surgical prosthetic devices, otherwise known as implants, is well known in various surgical applications, such as reconstructive surgery, for example, in the replacement of hip joints or the like. Use of surgical prosthetic devices such as plates, nails, pins, screws, and specially formed parts are commonly implanted into the skeletal structure of animals for the replacement of missing structural parts, or as permanent anchoring devices for maintaining a fixed relationship between the portions of a fractured bone. Rapid integration of these devices with the patient's natural bone, referred to as osseointegration, is desired, so that the strength of the interface is rapidly and maximally achieved. This reduces healing time, recovery time, and failure rate of the implant. These principles also apply to dental implants.

The application of cell adhesion domains (such as the RGD motif) to tissue engineering has become a subject of intense interest. The RGD (argininyl-glycinyl-aspartyl or Agr-Gly-Asp) tripeptide sequence (found in extracellular matrix clycoproteins such as type I collagen, bone sialoprotein [BSP], osteopontin, osteonectin, vitronectin, fibronectin, etc.) binds to cell surface integrins such as $\alpha_5\beta_3$ (reviewed by Butler, Connect. Tissue Res., 23:123–136, 1989 and Butler, J. Biol. Buccale, 19:83–89, 1991). Certain of these proteins may participate by acting as a seed or regulator of mineral crystal growth and/or by directing cells and their associated functions to specific sites within the tissue. The presence of the tripeptide sequence RGD, the distribution of these proteins, and their association with mineral suggest that these phosphoproteins may have a multifunctional role during mineralized tissue formation whereby they may, firstly, initiate and regulate mineralization, and secondly, direct dynamics by mediating cell attachment to the matrix (McKee et al., Anat. Rec., 234:479–492, 1992 and McKee et al., J. Bone Miner. Res., 8:485–496, 1992).

It is towards the identification of peptides capable of promoting bone mineralization and osseointegration of bone implants that the present invention is directed.

The citation of any reference herein should not be construed as an admission that such reference is available as "Prior Art" to the instant application.

SUMMARY OF THE INVENTION

In its broadest aspect, the invention is directed to the peptide YESENGEPRGDNYRAYEDEYSYFKG (SEQ ID NO:4) and fragments of YESENGEPRGDNYRAYEDEYSYFKG (SEQ ID NO:4) which include at least the sequence GEPRGD (SEQ ID NO;1). Thus, peptides of the invention may have the basic structure $X_1$EPRG$X_2$(SEQ ID NO:198), where $X_1$ is YESENG (SEQ ID NO:181) or any C-terminal segment thereof, and $X_2$ is DNYRAYEDEYSYFKG (SEQ ID NO:182)or any N-terminal segment thereof Selections of $X_1$ therefore include $_1$EPRGDNYRAY(SEQ ID NO:181), ESENG (SEQ ID NO:184), SENG (SEQ ID NO:185), ENG, NG, or G. Selections of $X_2$ include DNYRAYEDEYSYFKG (SEQ ID NO:182), DNYRAYEDEYSYFK (SEQ ID NO:187), DNYRAYEDEYSYF (SEQ ID NO:188), DNYRAYEDEYSY (SEQ ID NO:189), DNYRAYEDEYS (SEQ ID NO:190), DNYRAYEDEY (SEQ ID NO:191), DNYRAYEDE (SEQ ID NO:192), DNYRAYED (SEQ ID NO:193), DNYRAYE (SEQ ID NO:194), DNYRAY (SEQ ID NO:195), DNYRA (SEQ ID NO:196), DNYR (SEQ ID NO:197), DNY, DN, or D. $X_1$ and $X_2$ may be independently selected from the aforementioned selections.

Preferred peptides include GEPRGD (SEQ ID NO:1), ENGEPRGDNY (SEQ ID NO:2), YESENGEPRGDNYRAY (SEQ ID NO:3) and YESENGEPRGDNYRAYEDEYSYFKG (SEQ ID NO:4).

The aforementioned peptides may include at least one conservatively-substituted amino acid other than in the RGD sequence.

In another aspect of the invention, the peptides may have a C-terminal amide group. Thus, the invention embraces the peptide YESENGEPRGDNYRAYEDEYSYFKGamide (SEQ ID NO:8) and fragments of YESENGEPRGDNYRAYEDEYSYFKG (SEQ ID NO:4) which include at least the sequence GEPRGD (SEQ ID NO:1), and have a C-terminal amide. Thus, peptides of the invention may have the basic structure $X_1$EPRG$X_2$amide (SEQ ID NO:199), where $X_1$ is YESENG (SEQ ID NO:181) or any C-terminal segment thereof, and $X_2$ is DNYRAYEDEYSYFKG (SEQ ID NO:182) or any N-terminal segment thereof. Selections of $X_1$ therefore include (SEQ ID NO:181), ESENG (SEQ ID NO:184), SENG (SEQ ID NO:185), ENG, NG, or G. Selections of $X_2$ include DNYRAYEDEYSYFKG (SEQ ID NO:182), DNYRAYEDEYSYFK (SEQ ID NO:187), DNYRAYEDEYSYF (SEQ ID NO:188), DNYRAYEDEYSY (SEQ ID NO:1889), DNYRAYEDEYS (SEQ ID NO:190), DNYRAYEDEY (SEQ ID NO:191), DNYRAYEDE (SEQ ID NO:192), DNYRAYED (SEQ ID NO:193), DNYRAYE (SEQ ID NO:194), DNYRAY (SEQ ID NO:195), DNYRA (SEQ ID NO:196), DNYR (SEQ ID NO:197), DNY, DN, or D. $X_1$ and $X_2$ may be independently selected from the aforementioned selections.

The aforementioned peptides may include at least one conservatively-substituted amino acid other than in the RGD sequence.

Preferred embodiments include GEPRGDamide (SEQ ID NO:5), ENGEPRGDNYamide (SEQ ID NO:6), YESENGEPRGDNYRAYamide (SEQ ID NO:7) and YESENGEPRGDNYRAYEDEYSYFKGamide (SEQ ID NO:8).

In another aspect, the invention is directed to a pharmaceutical composition comprising the peptide YESENGEPRGDNYRAYEDEYSYFKG (SEQ ID NO:4), fragments of the sequence YESENGEPRGDNYRAYEDEYSYFKG (SEQ ID NO:4) comprising at least the sequence GEPRGD (SEQ ID NO:1), or any of the foregoing peptides comprising at least one conservative amino acid substitution other than in the RGD sequence; and a pharmaceutically acceptable carrier. Such peptides may include a C-terminal amide group. The carrier may be for example a gel or matrix, such as by way of non-limiting example polymcthylmethacrylate, polylactide/ polyglycolide, gelatin, or demineralized bone matrix. The peptide may be covalently bound to the carrier. The pharmaceutical composition may further include a growth factor, such as a bone morphogenetic protein. Non-limiting examples of such pharmaceutical compositions comprising the peptide include GEPRGD (SEQ ID NO:1), ENGEPRGDNY (SEQ ID NO:2), YESENGEPRGD-NYRAY (SEQ ID NO:3) or YESENGEPRGD-NYRAYEDEYSYFKG (SEQ ID NO:4), or a C-terminal amide of any of the foregoing, such as GEPRGDamide (SEQ ID NO:5), ENGEPRGDNYamide (SEQ ID NO:6), YESENGEPRGDNYRAYamide (SEQ ID NO:7) or YES-ENGEPRGDNYRAYEDEYSYFKGamide (SEQ ID NO:8).

In another aspect, the invention is directed to a composition for promoting bone mineralization comprising a bone matrix implant material and at least one peptide that is YESENGEPRGDNYRAYEDEYSYFKG (SEQ ID NO:4), a fragment of YESENGEPRGDNYRAYEDEYSYFKG (SEQ ID NO:4) comprising at least GEPRGD (SEQ ID NO:1), or any of the foregoing peptides which have at least one conservative amino acid substitution. Examples of suitable peptides, including those with C-terminal amide groups, are as described hereinabove. The implant material may be a titanium, demineralized bone matrix, coral bone substitute, or biopolymers. The composition may be coated on the implant material, or covalently bound to the implant material.

In a still further aspect of the invention, a method for promoting the mineralization of bone at a site within the body is provided, comprising administering to the site a pharmaceutical composition comprising the peptide YES-ENGEPRGDNYRAYEDEYSYFKG (SEQ ID NO:4), a fragment of YESENGEPRGDNYRAYEDEYSYFKG (SEQ ID NO:4) comprising at least GEPRGD (SEQ ID NO:1), or any of the foregoing peptides comprising at least one conservative amino acid substitution other than in the RGD sequence. The peptide may have a C-terminal amide group. The body may be an animal; vertebrate animals are preferred and humans most preferred. The aforementioned method may be used for a treatment such as but not limited to fracture repair, promoting bone ingrowth into a prosthesis, or promoting the integration of dental implants into bone. Non-limiting examples of suitable peptides include GEPRGD (SEQ ID NO:1), ENGEPRGDNY (SEQ ID NO:2), YESENGEPRGDNYRAY (SEQ ID NO:3), YES-ENGEPRGDNYRAYEDEYSYFKG (SEQ ID NO:4), GEPRGDamide (SEQ ID NO:5), ENGEPRGDNYamide (SEQ ID NO:6), YESENGEPRGDNYRAYamide (SEQ ID NO:7) or YESENGEPRGDNYRAYEDEYSYFKGamide (SEQ ID NO:8).

In yet a still further aspect of the invention, a method is provided for promoting the chemotaxis of bone-forming cells within the body to a substrate comprising applying to the substrate a pharmaceutical composition comprising the peptide YESENGEPRGDNYRAYEDEYSYFKG (SEQ ID NO:4) or a fragment of YESENGEPRGDNYRAYEDEY-SYFKG (SEQ ID NO:4) comprising at least GEPRGD (SEQ ID NO:1), or any of the foregoing peptides comprising at least one conservative amino acid substitution other than in the RGD sequence. The peptide may have a C-terminal amide group. Non-limiting examples are as described hereinabove. The substrate may be, for example, natural bone, a bone graft, demineralized bone matrix, or a bone prosthesis. The bone prosthesis may comprise titanium. The peptide may be covalently bound to the substrate. Non-limiting examples of useful peptides include GEPRGD (SEQ ID NO:1), ENGEPRGDNY (SEQ ID NO:2), YESEN-GEPRGDNYRAY (SEQ ID NO:3) or YESENGEPRGD-NYRAYEDEYSYFKG (SEQ ID NO:4). The peptide may have a C-terminal amide, such as GEPRGDamide (SEQ ID NO:5), ENGEPRGDNYamide (SEQ ID NO:6), YESEN-GEPRGDNYRAYamide (SEQ ID NO:7) or YESEN-GEPRGDNYRAYEDEYSYFKGamide (SEQ ID NO:8).

In another broad aspect of the invention, provided is a method for promoting the adhesion of bone-forming cells to a substrate comprising applying to the substrate a pharmaceutical composition comprising the peptide YESEN-GEPRGDNYRAYEDEYSYFKG (SEQ ID NO:4) or a fragment of YESENGEPRGDNYRAYEDEYSYFKG (SEQ ID NO:4) comprising at least GEPRGD (SEQ ID NO:1), or any of the foregoing peptides comprising at least one conservative amino acid substitution other than in the RGD sequence. The peptide may have a C-terminal amide group. Examples are as described hereinabove. The substrate may be, but is not limited to, natural bone, a bone graft, demineralized bone matrix, or a bone prosthesis. In one embodiment, the bone prosthesis substrate comprises titanium. The peptide may be covalently bound to the substrate.

In still a further aspect of the invention, a method is provided for promoting wound healing comprising administering to a wound site a pharmaceutical composition comprising the peptide YESENGEPRGDNYRAYEDEY-SYFKG (SEQ ID NO:4), a fragment of YESENGEPRGD-NYRAYEDEYSYFKG (SEQ ID NO:4) comprising at least GEPRGD (SEQ ID NO:1), or any of the foregoing peptides comprising at least one conservative amino acid substitution. Examples are as described above. The peptide may have a C-terminal amide group. The wound site may be a surgical wound, vascular graft, non-healing wounds or areas of non-union.

A further aspect of the invention is a method for inhibiting the metastasis of dysproliferative cells to a bone situs comprising administering to a mammal an effective dysproliferative cell adhesion or chemotaxis inhibitory dose of a pharmaceutical composition comprising the peptide YES-ENGEPRGDNYRAYEDEYSYFKG (SEQ ID NO:4), a fragment of YESENGEPRGDNYRAYEDEYSYFKG (SEQ ID NO:4), comprising at least GEPRGD (SEQ ID NO:1), or any of the foregoing peptides comprising at least one conservative amino acid substitution other than in the RGD sequence. The foregoing peptides with a C-terminal amide group are also embraced herein. Examples are as described hereinabove, including but not limited to GEPRGD (SEQ ID NO:1), ENGEPRGDNY (SEQ ID NO:2), YESEN-GEPRGDNYRAY (SEQ ID NO:3), YESENGEPRGD-NYRAYEDEYSYFKG (SEQ ID NO:4), GEPRGDamide (SEQ ID NO:5), ENGEPRGDNYamide (SEQ ID NO:6), YESENGEPRGDNYRAYamide (SEQ ID NO:7) or YES-ENGEPRGDNYRAYEDEYSYFKGamide (SEQ ID NO:8)

In yet another aspect of the invention, a method is provided for attracting and sequestering metastatic cells in the body comprising administering to the body a matrix comprising the peptide YESENGEPRGDNYRAYEDEY-SYFKG (SEQ ID NO:4), a fragment of YESENGEPRGD-NYRAYEDEYSYFKG (SEQ ID NO:4) comprising at least GEPRGD (SEQ ID NO:1), and any of the foregoing peptides comprising at least one conservative amino acid substitution other than in the RGD sequence. The peptide may have a C-terminal amide group. Non-limiting examples of suitable peptides and matrix components are those described hereinabove.

It is therefore an object of the invention to provide peptides capable of promoting bone mineralization and osseointegration of implants. The peptides may be provided in a pharmaceutical composition for application to a surgical site within the body, or covalently bound to an implant material.

It is a further object of the invention to provide peptides capable of attracting bone-forming cells to a desired site for the promotion of bone mineralization and osseointegration.

It is yet a further object of the invention to promote the adhesion of bone-forming cells to sites desirable of bone mineralization and integration.

It is another object of the invention to provide peptides capable of promoting wound healing, including that of vascular and skin grafts.

It is still yet a further object of the invention to provide a method for inhibiting the metastasis of cancer cells to bone sites by administering a peptide capable of blocking the localization of the metastatic cells to such sites. It is a further object to provide an implantable but easily removable matrix comprising a peptide capable of attracting and promoting the residence within the matrix of metastatic cells.

These and other aspects of the present invention will be better appreciated by reference to the following drawings and Detailed Description.

DETAILED DESCRIPTION OF THE INVENTION

Figure 1:
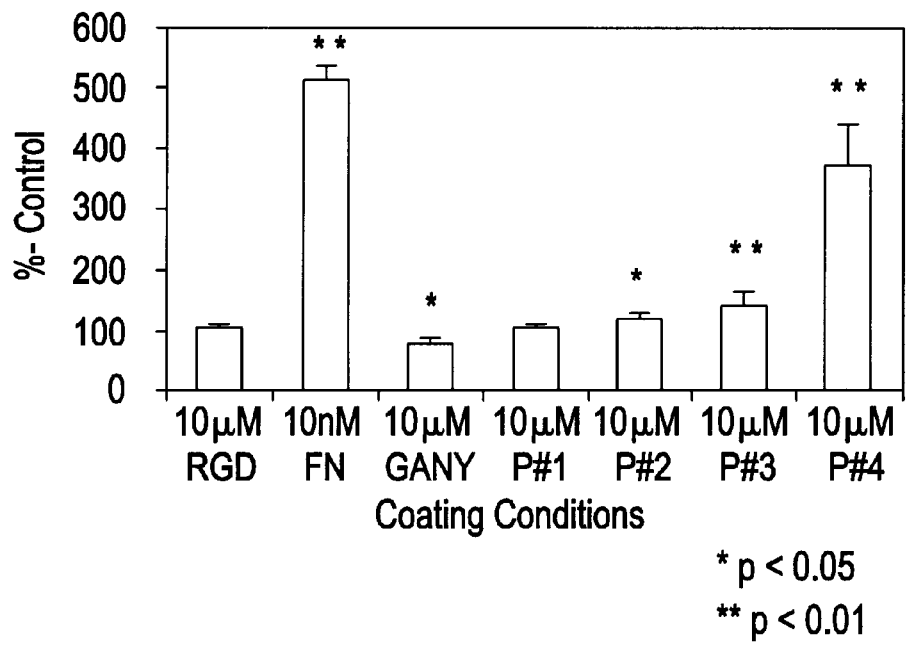
FIG. 1 depicts the results of a MC3T3 cell adhesion experiment using the peptides of the invention.

The inventors herein have designed, synthesized and performed adhesive and chemotactic characterizations of novel osteoblast binding peptides with potential for use on surfaces designed for osseointegration. As the peptides were synthesized using RINK resins for solid-phase synthesis using FMOC chemistry, the resulting peptides retained a C-terminal amide group, but this is not essential. RGDamide and GANYamide (SEQ ID NO:204) peptides were designed and synthesized as positive and negative control peptide sequences, respectively. As will be seen in the examples below, osteoblast adhesion experiments and MC3T3 chemotaxis experiments showed positive activity of the peptides. Based upon the enhanced properties of the aforementioned peptides, a variety of related peptides are useful for the purposes disclosed herein.

The amino acids of the peptides of the invention are set forth as their one-letter codes. The peptides of the invention include the peptide YESENGEPRGDNYRAYEDEYSYFKG (SEQ ID NO:4), fragments of YESENGEPRGDNYRAYEDEYSYFKG (SEQ ID NO:4) comprising at least GEPRGD (SEQ ID NO:1), or any of the foregoing peptides comprising at least one conservative amino acid substitution other than in the RGD sequence. Said in another way, the general structure of the peptides of the invention is X$_1$EPRGX$_2$(SEQ ID NO:198), where X$_1$ is YESENG (SEQ ID NO:181) or any C-terminal segment thereof, and X$_2$ is DNYRAYEDEYSYFKG (SEQ ID NO:182) or any N-terminal segment thereof. Such segments may have at least one conservative amino acid substitution, other than the N-terminal D in X$_2$. Selections of X$_1$ therefore include YESENG (SEQ ID NO:181), ESENG (SEQ ID NO:184), SENG (SEQ ID NO:185), ENG, NG, or G. Selections of X$_2$ include DNYRAYEDEYSYFKG (SEQ ID NO:182), DNYRAYEDEYSYFK (SEQ ID NO:187), DNYRAYEDEYSYF (SEQ ID NO:188), DNYRAYEDEYSY (SEQ ID NO:189), DNYRAYEDEYS (SEQ ID NO:190), DNYRAYEDEY (SEQ ID NO:191), DNYRAYEDE (SEQ ID NO:192), DNYRAYED (SEQ ID NO:193), DNYRAYE (SEQ ID NO:194), DNYRAY (SEQ ID NO:195), DNYRA (SEQ ID NO:196), DNYR (SEQ ID NO:197), DNY, DN, or D. As X$_1$ and X$_2$ may be independently selected from the aforementioned selections, a large number of peptides including YESENGEPRGDNYRAYEDEYSYFKG (SEQ ID NO:4) and fragments of YESENGEPRGDNYRAYEDEYSYFKG (SEQ ID NO:4) which include at least the sequence GEPRGD (SEQ ID NO:1) are included within the invention, namely:
YESENGEPRGDNYRAYEDEYSYFKG (SEQ ID No:4)
YESENGEPRGDNYRAYEDEYSYFK (SEQ ID No:9)
YESENGEPRGDNYRAYEDEYSYF (SEQ ID No:10)
YESENGEPRGDNYRAYEDEYSY (SEQ ID No:11)
YESENGEPRGDNYRAYEDEYS (SEQ ID No:12)
YESENGEPRGDNYRAYEDEY (SEQ ID No:13)
YESENGEPRGDNYRAYEDE (SEQ ID No:14)
YESENGEPRGDNYRAYED (SEQ ID No:15)
YESENGEPRGDNYRAYE (SEQ ID No:16)
YESENGEPRGDNYRAY (SEQ ID No:3)
YESENGEPRGDNYRA (SEQ ID No:17)
YESENGEPRGDNYR (SEQ ID No:18)
YESENGEPRGDNY (SEQ ID No:19)
YESENGEPRGDN (SEQ ID No:20)
YESENGEPRGD (SEQ ID No:21)
ESENGEPRGDNYRAYEDEYSYFKG (SEQ ID No:22)
ESENGEPRGDNYRAYEDEYSYFK (SEQ ID No:23)
ESENGEPRGDNYRAYEDEYSYF (SEQ ID No:24)
ESENGEPRGDNYRAYEDEYSY (SEQ ID No:25)
ESENGEPRGDNYRAYEDEYS (SEQ ID No:26)
ESENGEPRGDNYRAYEDEY (SEQ ID No:27)
ESENGEPRGDNYRAYEDE (SEQ ID No:28)
ESENGEPRGDNYRAYED (SEQ ID No:29)
ESENGEPRGDNYRAYE (SEQ ID No:30)
ESENGEPRGDNYRAY (SEQ ID No:31)
ESENGEPRGDNYRA (SEQ ID No:32)
ESENGEPRGDNYR (SEQ ID No:33)
ESENGEPRGDNY (SEQ ID No:34)
ESENGEPRGDN (SEQ ID No:35)
ESENGEPRGD (SEQ ID No:36)
SENGEPRGDNYRAYEDEYSYFKG (SEQ ID No:37)
SENGEPRGDNYRAYEDEYSYFK (SEQ ID No:38)
SENGEPRGDNYRAYEDEYSYF (SEQ ID No:39)
SENGEPRGDNYRAYEDEYSY (SEQ ID No:40)
SENGEPRGDNYRAYEDEYS (SEQ ID No:41)
SENGEPRGDNYRAYEDEY (SEQ ID No:42)
SENGEPRGDNYRAYEDE (SEQ ID No:43)
SENGEPRGDNYRAYED (SEQ ID No:44)
SENGEPRGDNYRAYE (SEQ ID No:45)
SENGEPRGDNYRAY (SEQ ID No:46)
SENGEPRGDNYRA (SEQ ID No:47)
SENGEPRGDNYR (SEQ ID No:48)
SENGEPRGDNY (SEQ ID No:49)
SENGEPRGDN (SEQ ID No:50)
SENGEPRGD (SEQ ID No:51)
ENGEPRGDNYRAYEDEYSYFKG (SEQ ID No:52)
ENGEPRGDNYRAYEDEYSYFK (SEQ ID No:53)
ENGEPRGDNYRAYEDEYSYF (SEQ ID No:54)
ENGEPRGDNYRAYEDEYSY (SEQ ID No:55)
ENGEPRGDNYRAYEDEYS (SEQ ID No:56)
ENGEPRGDNYRAYEDEY (SEQ ID No:57)
ENGEPRGDNYRAYEDE (SEQ ID No:58)
ENGEPRGDNYRAYED (SEQ ID No:59)
ENGEPRGDNYRAYE (SEQ ID No:60)
ENGEPRGDNYRAY (SEQ ID No:61)
ENGEPRGDNYRA (SEQ ID No:62)
ENGEPRGDNYR (SEQ ID No:63)
ENGEPRGDNY (SEQ ID No:2)
ENGEPRGDN (SEQ ID No:64)
ENGEPRGD (SEQ ID No:65)

NGEPRGDNYRAYEDEYSYFKG (SEQ ID No:66)
NGEPRGDNYRAYEDEYSYFK (SEQ ID No:67)
NGEPRGDNYRAYEDEYSYF (SEQ ID No:68)
NGEPRGDNYRAYEDEYSY (SEQ ID No:69)
NGEPRGDNYRAYEDEYS (SEQ ID No:70)
NGEPRGDNYRAYEDEY (SEQ ID No:71)
NGEPRGDNYRAYEDE (SEQ ID No:72)
NGEPRGDNYRAYED (SEQ ID No:73)
NGEPRGDNYRAYE (SEQ ID No:74)
NGEPRGDNYRAY (SEQ ID No:75)
NGEPRGDNYRA (SEQ ID No:76)
NGEPRGDNYR (SEQ ID No:77)
NGEPRGDNY (SEQ ID No:78)
NGEPRGDN (SEQ ID No:79)
NGEPRGD (SEQ ID No:80)
GEPRGDNYRAYEDEYSYFKG (SEQ ID No:81)
GEPRGDNYRAYEDEYSYFK (SEQ ID No:82)
GEPRGDNYRAYEDEYSYF (SEQ ID No:83)
GEPRGDNYRAYEDEYSY (SEQ ID No:84)
GEPRGDNYRAYEDEYS (SEQ ID No:85)
GEPRGDNYRAYEDEY (SEQ ID No:86)
GEPRGDNYRAYEDE (SEQ ID No:87)
GEPRGDNYRAYED (SEQ ID No:88)
GEPRGDNYRAYE (SEQ ID No:89)
GEPRGDNYRAY (SEQ ID No:90)
GEPRGDNYRA (SEQ ID No:91)
GEPRGDNYR (SEQ ID No:92)
GEPRGDNY (SEQ ID No:93)
GEPRGDN (SEQ ID No:94) and
GEPRGD (SEQ ID No:1).

As noted above, these peptides may be in the form of an amide, namely,
YESENGEPRGDNYRAYEDEYSYFKGamide (SEQ ID No:8)
YESENGEPRGDNYRAYEDEYSYFKamide (SEQ ID No:95)
YESENGEPRGDNYRAYEDEYSYFamide (SEQ ID No:96)
YESENGEPRGDNYRAYEDEYSYamide (SEQ ID No:97)
YESENGEPRGDNYRAYEDEYSamide (SEQ ID No:98)
YESENGEPRGDNYRAYEDEYamide (SEQ ID No:99)
YESENGEPRGDNYRAYEDEamide (SEQ ID No:100)
YESENGEPRGDNYRAYEDamide (SEQ ID No:101)
YESENGEPRGDNYRAYEamide (SEQ ID No:102)
YESENGEPRGDNYRAYamide (SEQ ID No:7)
YESENGEPRGDNYRAamide (SEQ ID No:103)
YESENGEPRGDNYRamide (SEQ ID No:104)
YESENGEPRGDNYamide (SEQ ID No:105)
YESENGEPRGDNamide (SEQ ID No:106)
YESENGEPRGDamide (SEQ ID No:107)
ESENGEPRGDNYRAYEDEYSYFKGamide (SEQ ID No:108)
ESENGEPRGDNYRAYEDEYSYFKamide (SEQ ID No:109)
ESENGEPRGDNYRAYEDEYSYFamide (SEQ ID No:110)
ESENGEPRGDNYRAYEDEYSYamide (SEQ ID No:111)
ESENGEPRGDNYRAYEDEYSamide (SEQ ID No:112)
ESENGEPRGDNYRAYEDEYamide (SEQ ID No:113)
ESENGEPRGDNYRAYEDEamide (SEQ ID No:114)
ESENGEPRGDNYRAYEDamide (SEQ ID No:115)
ESENGEPRGDNYRAYEamide (SEQ ID No:116)
ESENGEPRGDNYRAYamide (SEQ ID No:117)
ESENGEPRGDNYRAamide (SEQ ID No:118)
ESENGEPRGDNYRamide (SEQ ID No:119)
ESENGEPRGDNYamide (SEQ ID No:120)
ESENGEPRGDNamide (SEQ ID No:121)
ESENGEPRGDamide (SEQ ID No:122)
SENGEPRGDNYRAYEDEYSYFKGamide (SEQ ID No:123)
SENGEPRGDNYRAYEDEYSYFKamide (SEQ ID No:124)
SENGEPRGDNYRAYEDEYSYFamide (SEQ ID No:125)
SENGEPRGDNYRAYEDEYSYamide (SEQ ID No:126)
SENGEPRGDNYRAYEDEYSamide (SEQ ID No:127)
SENGEPRGDNYRAYEDEYamide (SEQ ID No:128)
SENGEPRGDNYRAYEDEamide (SEQ ID No:129)
SENGEPRGDNYRAYEDamide (SEQ ID No:130)
SENGEPRGDNYRAYEamide (SEQ ID No:131)
SENGEPRGDNYRAYamide (SEQ ID No:132)
SENGEPRGDNYRAamide (SEQ ID No:133)
SENGEPRGDNYRamide (SEQ ID No:134)
SENGEPRGDNYamide (SEQ ID No:135)
SENGEPRGDNamide (SEQ ID No:136)
SENGEPRGDamide (SEQ ID No:137)
ENGEPRGDNYRAYEDEYSYFKGamide (SEQ ID No:138)
ENGEPRGDNYRAYEDEYSYFKamide (SEQ ID No:139)
ENGEPRGDNYRAYEDEYSYFamide (SEQ ID No:140)
ENGEPRGDNYRAYEDEYSYamide (SEQ ID No:141)
ENGEPRGDNYRAYEDEYSamide (SEQ ID No:142)
ENGEPRGDNYRAYEDEYamide (SEQ ID No:143}
ENGEPRGDNYRAYEDEamide (SEQ ID No:144)
ENGEPRGDNYRAYEDamide (SEQ ID No:145)
ENGEPRGDNYRAYEamide (SEQ ID No:146)
ENGEPRGDNYRAYamide (SEQ ID No:147)
ENGEPRGDNYRAamide (SEQ ID No:148)
ENGEPRGDNYRamide (SEQ ID No:149)
ENGEPRGDNYamide (SEQ ID No:6)
ENGEPRGDNamide (SEQ ID No:150)
ENGEPRGDamide (SEQ ID No:151)
NGEPRGDNYRAYEDEYSYFKGamide (SEQ ID No:152)
NGEPRGDNYRAYEDEYSYFKamide (SEQ ID No:153)
NGEPRGDNYRAYEDEYSYFamide (SEQ ID No:154)
NGEPRGDNYRAYEDEYSYamide (SEQ ID No:155)
NGEPRGDNYRAYEDEYSamide (SEQ ID No:156)
NGEPRGDNYRAYEDEYamide (SEQ ID No:157)
NGEPRGDNYRAYEDEamide (SEQ ID No:158)
NGEPRGDNYRAYEDamide (SEQ ID No:159)
NGEPRGDNYRAYEamide (SEQ ID No:160)
NGEPRGDNYRAYamide (SEQ ID No:161)
NGEPRGDNYRAamide (SEQ ID No:162)
NGEPRGDNYRamide (SEQ ID No:163)
NGEPRGDNYamide (SEQ ID No:164)
NGEPRGDNamide (SEQ ID No:165)
NGEPRGDamide (SEQ ID No:166)
GEPRGDNYRAYEDEYSYFKGamide (SEQ ID No:167)
GEPRGDNYRAYEDEYSYFKamide (SEQ ID No:168)
GEPRGDNYRAYEDEYSYFamide (SEQ ID No:169)
GEPRGDNYRAYEDEYSYamide (SEQ ID No:170)
GEPRGDNYRAYEDEYSamide (SEQ ID No:171)
GEPRGDNYRAYEDEYamide (SEQ ID No:172)
GEPRGDNYRAYEDEamide (SEQ ID No:173)
GEPRGDNYRAYEDamide (SEQ ID No:174)
GEPRGDNYRAYEamide (SEQ ID No:175)
GEPRGDNYRAYamide (SEQ ID No:176)
GEPRGDNYRAamide (SEQ ID No:177)
GEPRGDNYRamide (SEQ ID No:178)
GEPRGDNYamide (SEQ ID No:179)
GEPRGDNamide (SEQ ID No:180), and
GEPRGDamide (SEQ ID No:5).

The peptides of the invention may for convenience be divided into the following groups. For example, the peptide may comprise the sequence $X_1$EPRGD (SEQ ID NO:200), wherein $X_1$ is YESENG (SEQ ID NO:181) or any C-terminal segment thereof. Examples include the peptides YESENGEPRGD (SEQ ID NO:21), ESENGEPRGD (SEQ ID NO:36), SENGEPRGD (SEQ ID NO:51), ENGEPRGD (SEQ ID NO:65), NGEPRGD (SEQ ID NO:80), and GEPRGD (SEQ ID NO:1). In another aspect, the peptide may comprise the sequence $X_1$EPRGDNY (SEQ ID NO:201), wherein $X_1$ is YESENG (SEQ ID NO:181) or any C-terminal segment thereof. Examples include the peptides YESENGEPRGDNY (SEQ ID NO:19), ESENGEPRGDNY (SEQ ID NO:2), SENGEPRGDNY (SEQ ID NO:49), ENGEPRGDNY (SEQ ID NO:2), NGEPRGDNY (SEQ ID NO:78), and GEPRGDNY (SEQ ID NO:93). By way of further example, the peptides may comprise the sequence GEPRGDX$_2$ (SEQ ID NO:201), wherein $X_2$ is NYRAYEDEYSYFKG (SEQ ID NO:202) or any N-terminal segment thereof. Examples include GEPRGD-NYRAYEDEYSYFK (SEQ ID NO:81), GEPRGD-NYRAYEDEYSYF (SEQ ID NO:83), GEPRGD-NYRAYEDEYSY (SEQ ID NO:84), GEPRGDNYRAYEDEYS (SEQ ID NO:85), GEPRGD-NYRAYEDEY (SEQ ID NO:86), GEPRGDNYRAYEDE (SEQ ID NO:87), GEPRGDNYRAYED (SEQ ID NO:88), GEPRGDNYRAYE (SEQ ID NO:89), GEPRGDNYRAY (SEQ ID NO:90), GEPRGDNYRA (SEQ ID NO:91), GEPRGDNYR (SEQ ID NO:92), GEPRGDNY (SEQ ID NO:93), and GEPRGDN (SEQ ID NO:94). In a further example, peptides of the invention comprise the sequence $X_1$EPRGDNYRAY (SEQ ID NO:206) wherein $X_1$ is YES-ENG (SEQ ID NO:181) or an N-terminal segment thereof. Examples include YESENGEPRGDNYRAY (SEQ ID NO:3), ESENGEPRGDNYRAY (SEQ ID NO:31), SEN-GEPRGDNYRAY (SEQ ID NO:46), ENGEPRGDNYRAY (SEQ ID NO:61), NGEPRGDNYRAY (SEQ ID NO:75), and GEPRGDNYRAY (SEQ ID NO:90). In yet a further aspect, peptides comprise the sequence YESENGEPRGD-NYRAYX$_3$ (SEQ ID NO:186) wherein $X_3$ is EDEYSYFKG (SEQ ID NO:203) or an N-terminal segment thereof. Examples include YESENGEPRGDNYRAYEDEYSYFKG (SEQ ID NO:4), YESENGEPRGDNYRAYEDEYSYFK (SEQ ID NO:9),YESENGEPRGDNYRAYEDEYSYF (SEQ ID NO:10), YESENGEPRGDNYRAYEDEYSY (SEQ ID NO:11), YESENGEPRGDNYRAYEDEYS (SEQ ID NO:12), YESENGEPRGDNYRAYEDEY (SEQ ID NO:13), YESENGEPRGDNYRAYEDE (SEQ ID NO:14), YESENGEPRGDNYRAYED (SEQ ID NO:15), and YES-ENGEPRGDNYRAYE (SEQ ID NO:16). The aforementioned peptides are only examples of various other peptides which comprise the basic structure $X_1$EPRGX$_2$ (SEQ ID !NO:198), where $X_1$ is YESENG (SEQ ID NO:181) or any C-terminal segment thereof, and $X_2$ is DNYRAYEDEYSY-FKG (SEQ ID NO:182) or any N-terminal segment thereof. The foregoing examples with a C-terminal amide group are also embraced herein.

The peptides of the invention may include at least one conservative amino acid substitution other than in the RGD sequence and retain the chemoattractant or adhesion properties of the peptide. Such functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Furthermore, the peptides of the invention may have a chemical modification or moiety and retain biological activity. In particular, compounds prepared using a RINK resin may have a C-terminal amide group.

Various methods may be used to prepare the peptides of the invention. Synthetic polypeptides, prepared using the well known techniques of solid phase, liquid phase, or peptide condensation techniques, or any combination thereof, can include natural and unnatural amino acids. Amino acids used for peptide synthesis may be standard BOC ($N^\alpha$-amino protected $N^\alpha$-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile $N^\alpha$-amino protected 9-fluorenylmethoxycarbonyl (FMOC) amino acids first described by Carpino and Han (1972, J. Org. Chem. 37:3403–3409). Both FMOC and BOC $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by Applied BioSystems and Advanced ChemTech.

The present invention is further directed to pharmaceutical compositions comprising the aforementioned peptides. Various compositions may be used for the various applications and uses of the peptide. In the instance where the peptide is applied to a bone implant, the peptide may be formulated in a sterile gel or putty to facilitate surgical application of the material to the desired site. Such gels of putties may be prepared from materials known to the skilled artisan, such as demineralized bone matrix. Numerous other variations in the form of the peptide of the invention in te pharmaceutical composition are embraced herein. As will be elaborated below, the peptide may be covalently bound to components in the gel or putty. Various gels or putties are available for such uses. Also, the use of liposomes, microcapsules or microspheres, inclusion complexes, or other types of carriers is contemplated. Thus, the agent may be microencapsulated or provided in a slow-release formulation. Other components of the pharmaceutical composition may include pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435–1712 which arc herein incorporated by reference. The compositions may be prepared in liquid form, or may be in dried powder, such as lyophilized form.

A subject in whom administration of a peptide of the invention is an effective therapeutic regiment for promoting bone mineralization is most preferably a human, preferably any vertebrate animal, and embraces any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In the instance in which the peptide of the invention is covalently bound to the carrier, or to the implant as described further below, various chemical linking methods may be employed to effect a covalent bond between a moiety of the peptide, such as an amino or carboxyl group, and a likewise derivatizable group on the carrier or implant matrix. For example, an implant may have carboxyl-functional groups such as is described in U.S. Pat. No. 5,866,113, incorporated herein by reference, to which an amino group of the peptide may be coupled using, for example, a carbodiimide. A metal implant may have derivatizable groups, for example, see U.S. Pat. No. 5,876,454.

The aforementioned matrix comprising a peptide of the invention may further include a growth factor which in combination with the peptide further promotes the mineralization process and osseointegration. Examples include bone morphogenetic proteins such as osteocalcin, beta transforming growth factor, insulin-like growth factor, platelet-derived growth factor, and basic fibroblast growth factor, etc. These may also be covalently bound to the matrix.

The present invention is also directed to a composition for promoting bone mineralization comprising a bone matrix implant material and at least one of the aforementioned peptides. For example, a titanium bone prosthesis coated noncovalently or bound covalently with a peptide of the invention provides a surface to which bone-forming cells are attracted, adhere, and begin the mineralization process. Such materials include, for example, demineralized bone matrix, coral bone substitute, and various biopolymers. As noted above, the peptide in a particular composition may be coated on the implant; alternatively it may be covalently bound using chemistry such as described above.

The aforementioned peptides and pharmaceutical compositions containing them are useful for several purposes related to enhancing the process of bone mineralization, osseointegration, wound healing, vascular graft healing, and related processes in which cells are recruited to the site undergoing repair, adhering thereto and initiating, in the case of bone, the mineralization process. The present invention provides a method for promoting the mineralization of bone at a site within the body by administering to the site a pharmaceutical composition comprising a peptide selected from the group consisting of the sequence YESENGEPRGDNYRAYEDEYSYFKG (SEQ ID NO:4), a fragment of said sequence including at least GEPRGD (SEQ ID NO:1), and any of the foregoing peptides comprising at least one conservative amino acid substitution. The peptide may have a C-terminal amide group. While humans are the most preferred subjects for the method, vertebrate animals are preferred and any animal is a potential subject. Veterinary uses are also preferred. These methods may be used for purposes such as aiding in the repair of broken bones, i.e., compound and various other types of fractures, particularly those requiring surgical intervention for repair, and more particularly those in which an implant or other hardware is used to aid in the repair. The pharmaceutical compositions comprising peptides of the invention are used in combination with the aforementioned hardware used to reconstruct or strengthen fracture repairs. The methods may be used to promote bone ingrowth into the porous portions of bone and other implants, including dental implants.

The invention is further directed to various aspects of the process of bone mineralization, including chemotaxis of bone-forming cells within the body to the site of bone repair, and adhesion of the bone-forming cells to the site. As will be shown in the examples below, the peptides of the invention provide significantly enhanced chemotaxis and adherence properties as compared with the peptide RGD. In these examples, all of the peptides tested, including the controls, were in the amide form, as this is the product of solid-phase synthesis, but the carboxy forms of the peptides as well as other chemical modifications arc also embraced by the present invention. The types of surfaces to which the bone-forming cells are attracted and may adhere include, but are not limited to, natural bone, a bone graft, demineralized bone matrix, or a bone prosthesis. In one preferred embodiment, the bone prosthesis comprises titanium. The peptide may be covalently bound to the implant surface, or coated thereon.

Examples of useful peptides for the aforementioned purposes include all of those peptides described above, i.e., the peptide YESENGEPRGDNYRAYEDEYSYFKG (SEQ ID NO:4) or fragments of YESENGEPRGDNYRAYEDEYSYFKG (SEQ ID NO:4) comprising at least GEPRGD (SEQ ID NO:1), or any of the foregoing peptides comprising at least one conservative amino acid substitution. A C-terminal amide group may also be present. Said in another way, the general structure of the peptides useful for the methods herein is $X_1EPRGX_2$ (SEQ ID NO:198) or $X_1EPRGX_2$amide (SEQ ID NO:199), where $X_1$ is YESENG (SEQ ID NO:181) or any C-terminal segment thereof, and $X_2$ is DNYRAYEDEYSYFKG (SEQ ID NO:1 82) or any N-terminal segment thereof. By way of non-limiting examples, the peptide may be GEPRGD (SEQ ID NO:1), ENGEPRGDNYRAY (SEQ ID NO:2), YESENGEPRGDNYRAY (SEQ ID NO:3), YESENGEPRGDNYRAYEDEYSYFKG (SEQ ID NO:4), GEPRGDamide (SEQ ID NO:5), ENGEPRGDNYamide (SEQ ID NO:6), YESENGEPRGDNYRAYamide (SEQ ID NO:7) or YESENGEPRGDNYRAYEDEYSYFKGamide (SEQ ID NO:8). These peptides in the form of amides are also examples of useful peptides for the aforementioned purposes.

In another aspect of the invention, a substrate such as a bone implant or natural bone may be modified to improve adhesion of bone-forming cells by applying to the substrate a pharmaceutical composition comprising a peptide selected from the group consisting of the sequence YESENGEPRGDNYRAYEDEYSYFKG (SEQ ID NO:4), a fragment of said sequence comprising at least GEPRGD (SEQ ID NO:1), or any of the foregoing peptides comprising at least one conservative amino acid substitution. A C-terminal amide group may be present. The substrate may be, by way of non-limiting example, natural bone, a bone graft, demineralized bone matrix, or a bone prosthesis. In a preferred embodiment, the bone prosthesis comprises titanium.

In a further aspect of the invention and exploitation of the chemoattractiveness and adhesion-promoting properties of the peptides herein, a method is provided for promoting wound healing comprising administering to a wound site a pharmaceutical composition comprising a peptide as described above. The wound site may be a surgical wound, vascular graft, skin graft, non-healing wounds or areas of non-union. The peptides herein promote the migration and attachment of cells such as fibroblasts and fibrocytes to the wound and enhance the process of wound repair. The composition may also include other agents which further promote healing, including growth factors.

Another aspect of the invention addresses the propensity for certain dysproliferative cells, in particular metastatic cancer cells, of metastasizing from a primary tumor to a location in bone. As the peptides of the present invention if provided at the site of a bone implant or natural bone enhance migration of bone-forming cells to the site, likewise, the systemic administration of a peptide of the invention will compete with the RGD sites in bone and reduce bone metastasis.

The peptide of the invention may be administered by parenteral or oral means, by way of a formulation that provides a high degree of bioavailability of the peptide in the body. By way of example, injectable formulations, slow-release formulation, and oral formulations in which the peptide of the invention is protected from hydrolysis by digestive enzymes before absorption are embraced herein. Treatment of a cancer patient with a tumor with a propensity for metastasis to bone is a preferred use of this aspect of the invention.

By similar fashion to the above-mentioned use of the peptides of the invention, a further and related method is to provide a readily accessible site in a patient to which metastatic cancer cells will be attracted and can be removed readily and/or periodically from the body. For example, a matrix comprising a peptide of the invention provided, by way of non-limiting example, subcutaneously or intraperitoneally, will attract and promote the adhesion of dysproliferative cells attracted by receptor proteins recognizing the RGD site. The implanted matrix may serve as a type of biological filter to capture cells released into the circulation from the primary tumor, in particular during surgical procedures during which such release may be increased. The matrix may be removed or replenished periodically, particularly before it undergoes atopic mineralization.

While not wishing to be bound to theory, the bone-forming cells that are believed to be attracted to the peptides of the instant invention, and are promoted to adhere once attracted, are cells known as osteoblasts. These cells are the principal bone-forming cells in the body. For the purposes of this discussion, bone shall be defined as the tissue that is formed by mineral deposition within a framework of collagen. Mineral is a form of carbonated hydroxyapatite. The collagen mentioned above for these purposes is type I collagen.

The histologic features of the bone forming cells (osteoblasts) belie their high anabolic activity. They have a very extensive rough endoplasmic reticulum composed of polysomal structures. Proteins being produced by these bone-forming cells include type I collagen and other non-collagenous proteins, such as osteocalcin, regulatory factors such as bone morphogenetic proteins, beta transforming growth factors, insulin-like growth factors, platelet-derived growth factors, and basic fibroblast growth factors, among others.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Preparation of Peptides of the Invention

Using Chou-Fasman predictive calculations (Chou and Fasman: Biochemistry 13:211–222, 1974) of secondary protein structure of human-like sequences culled from the RGD domain sequence of hBSP and armed with the knowledge of the RGD domain structure and the importance of tyrosine flanking regions (Stubbs et al.: JBMR 12(8):1210–1222, 1997), the following sequences were designed which would promote a firm β-turn structure in the region of -P285-R286-G287-D288-, i.e., GEPRGDamide (SEQ ID NO:5), ENGEPRGDNYamide (SEQ ID NO:6), YESENGEPRGDNYPAYamide (SEQ ID NO:7) and YESENGEPRGDNYRAYEDEYSYFKGamide (SEQ ID NO:8). RGDamide and GANYamide (SEQ ID NO:204) were designed and synthesized as positive and negative control peptide sequences respectively. Syntheses were performed on RINK resins using standard FMOC chemistry. Peptide make-up was confirmed by amino acid analysis and HPLC.

EXAMPLE 2

Promotion of Osteoblast Adhesion by Peptides of the Invention

Osteoblast adhesion experiments were performed in peptide precoated polystyrene 96 well non-tissue culture plates with MC3T3 murine osteoblasts as follows: 1) precoating was performed with 100 $\mu$l of control peptides, fibronectin (FN) and experimental peptides (at 1–250 $\mu$M) for 24 hours, aspirated and plate rinsed twice with 1× phosphate buffered saline (PBS); 2) plates were after-coated with 100 $\mu$l/well of 1 mg/ml bovine serum albumin (BSA) in PBS for 2 hours at 37° C./5%$CO_2$; 3) early passage MC3T3 cells (30,000 cells in 100 $\mu$l/well) in serum-free modified Eagles Medium-α (MEM-α) with penicillin/streptomycin and incubated for 2 hours at 37° C./5%$CO_2$; 4) wells were then aspirated and rinsed gently three times with 1× PBS; and 5) cell adhesion was measured using the N-acetyl-hexosaminidase activity assay and confirmed by manual counting after trypsinization.

As shown in FIG. 1, novel peptides (P#1 to P#4, SEQ ID Nos. 5–8, respectively) significantly enhanced adhesion of MC3T3 cells to polystyrene plates ($p<0.05$) relative to no peptide precoating. RGDamide and GEPRGDamide (peptide SEQ ID NO:5) were not stimulatory at this pre-coating concentration (10 $\mu$M), however, peptide SEQ ID NO:5 did enhance adhesion (as did RGDamide, though to a lesser degree) when precoating concentrations of 100 µM to 250 µM were used. The use of these higher precoating concentrations also resulted in adhesion enhancement by peptide SEQ ID NO:7 that was equal to that of peptide SEQ ID NO:8. Peptide SEQ ID NO:8 was by far the most adhesion-enhancing synthetic peptide (p<0.001) rivaling the enhancement induced by the optimal precoating concentration of fibronectin (FN). GANYamide inhibited MC3T3 adhesion under these conditions.

EXAMPLE 3

Promotion of Osteoblast Migration by Peptides of the Invention

MC3T3 chemotaxis experiments were carried out in 48-well Boyden chambers as follows: 1) 30 µl of control solution, FN solution or experimental peptide in solution was placed into U-shaped wells; 2) 50,000 cells (in 50 µl) were added atop filters with 5 µm pores; 3) chambers were then incubated at 37° C./5%$CO_2$ for 18 hours; and 4) MC3T3 cells which had migrated were stained and visually counted with a light microscope, taking the average number of cells/5 fields (400×mag.)

Figure 2:
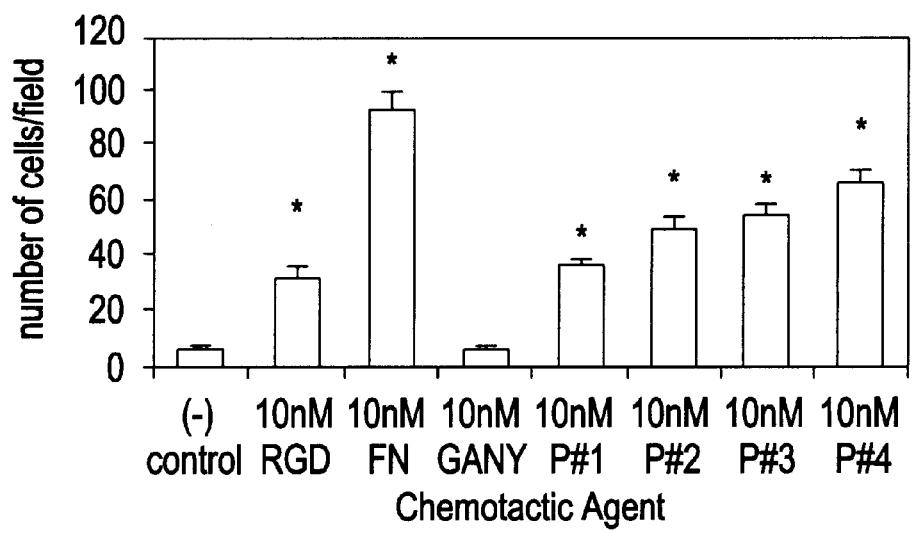
FIG. 2 depicts the results of a MC3T3 cell chemotaxis experiment using the peptides of the invention.

Novel peptides #'s 1–4 (SEQ ID No:5–8, respectively) acted as significant chemoattractants for MC3T3 cells (greater than RGDamide) and the extent of this enhancement increased with the size of the peptides (FIG. 2). GANYamide (SEQ ID NO:204; the negative control peptide) was not stimulatory.

Dose-response studies were performed with peptides SEQ ID Nos. 6 and 7. At 1 µM, peptide SEQ ID NO:6 showed a 40% increase over control migration level, and at 10 nM a 61% increase, showing increased potency at lower doses. By comparison, RGDamide was 60% above control at 100 nM. Peptide SEQ ID NO:7 at 1 µM showed an 11% increase over control, but at 10 nM was 33% over control, also showing increased potency at a lower dose.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A method for promoting the mineralization of bone at a site within the body comprising administering to said site a pharmaceutical composition comprising a peptide selected from the group consisting of the sequence YESENGEPRGDNYRAYEDEYSYFKG (SEQ ID NO:4), a fragment of said sequence comprising at least GEPRGD (SEQ ID NO:1), any of the foregoing peptides Faith a C-terminal amide group, and any of the foregoing peptides comprising at least one conservative amino acid substitution other than in the RGD sequence.

2. The method of claim 1 wherein said body is a vertebrate body.

3. The method of claim 1 used for a treatment selected from the group consisting of fracture repair, promoting bone ingrowth into a prosthesis, promoting union of an area of non-union, promote healing of non-healing wounds, and promoting the integration of dental implants into bone.

4. The method of claim 1 wherein said peptide is GEPRGD (SEQ ID NO:1), ENGEPRGDNY (SEQ ID NO:2), YESENGEPRGDNYRAY (SEQ ID NO:3), YESENGEPRGDNYRAYEDEYSYFKG (SEQ ID NO:4), or a C-terminal amide of any of the foregoing.

* * * * *

```
                           SEQUENCE LISTING

<160> NUMBER OF SEQ ID NOS:  180

<210> SEQ ID NO 1
   <211> LENGTH: 6
   <212> TYPE: PRT
   <213> ORGANISM: Homo sapiens
   <220> FEATURE:
   <223> OTHER INFORMATION: Fragment peptide from bone sialoprotein (BSP).

<400> SEQUENCE: 1

Gly Glu Pro Arg Gly Asp
   1               5

<210> SEQ ID NO 2
   <211> LENGTH: 10
   <212> TYPE: PRT
   <213> ORGANISM: Homo sapiens
   <220> FEATURE:
   <223> OTHER INFORMATION: Fragment peptide from bone sialoprotein (BSP).

<400> SEQUENCE: 2

Glu Asn Gly Glu Pro Arg Gly Asp Asn Tyr
   1               5                   10

<210> SEQ ID NO 3
   <211> LENGTH: 16
   <212> TYPE: PRT
   <213> ORGANISM: Homo sapiens
   <220> FEATURE:
   <223> OTHER INFORMATION: Fragment peptide from bone sialoprotein (BSP).

<400> SEQUENCE: 3

Tyr Glu Ser Glu Asn Gly Glu Pro Arg Gly Asp Asn Tyr Arg Ala Tyr
   1               5                   10                  15

<210> SEQ ID NO 4
   <211> LENGTH: 25
   <212> TYPE: PRT
   <213> ORGANISM: Homo sapiens
   <220> FEATURE:
```

```
-continued

<223> OTHER INFORMATION: Fragment peptide from bone sialoprotein (BSP).

<400> SEQUENCE: 4

Tyr Glu Ser Glu Asn Gly Glu Pro Arg Gly Asp Asn Tyr Arg Ala Tyr
 1               5                  10                  15

Glu Asp Glu Tyr Ser Tyr Phe Lys Gly
            20                  25

<210> SEQ ID NO 5
<211> LENGTH: 6
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 5

Gly Glu Pro Arg Gly Asp
 1               5

<210> SEQ ID NO 6
<211> LENGTH: 10
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 6

Glu Asn Gly Glu Pro Arg Gly Asp Asn Tyr
 1               5                  10

<210> SEQ ID NO 7
<211> LENGTH: 16
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 7

Tyr Glu Ser Glu Asn Gly Glu Pro Arg Gly Asp Asn Tyr Arg Ala Tyr
 1               5                  10                  15

<210> SEQ ID NO 8
<211> LENGTH: 25
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 8

Tyr Glu Ser Glu Asn Gly Glu Pro Arg Gly Asp Asn Tyr Arg Ala Tyr
 1               5                  10                  15

Glu Asp Glu Tyr Ser Tyr Phe Lys Gly
            20                  25

<210> SEQ ID NO 9
<211> LENGTH: 24
<212> TYPE: PRT
<213> ORGANISM: Homo sapiens
<220> FEATURE:
<223> OTHER INFORMATION: Fragment peptide from bone sialoprotein (BSP).
```

```
<400> SEQUENCE: 9

Tyr Glu Ser Glu Asn Gly Glu Pro Arg Gly Asp Asn Tyr Arg Ala Tyr
 1               5                  10                  15

Glu Asp Glu Tyr Ser Tyr Phe Lys
             20

<210> SEQ ID NO 10
<211> LENGTH: 23
<212> TYPE: PRT
<213> ORGANISM: Homo sapiens
<220> FEATURE:
<223> OTHER INFORMATION: Fragment peptide from bone sialoprotein (BSP).

<400> SEQUENCE: 10

Tyr Glu Ser Glu Asn Gly Glu Pro Arg Gly Asp Asn Tyr Arg Ala Tyr
 1               5                  10                  15

Glu Asp Glu Tyr Ser Tyr Phe
             20

<210> SEQ ID NO 11
<211> LENGTH: 22
<212> TYPE: PRT
<213> ORGANISM: Homo sapiens
<220> FEATURE:
<223> OTHER INFORMATION: Fragment peptide from bone sialoprotein (BSP).

<400> SEQUENCE: 11

Tyr Glu Ser Glu Asn Gly Glu Pro Arg Gly Asp Asn Tyr Arg Ala Tyr
 1               5                  10                  15

Glu Asp Glu Tyr Ser Tyr
             20

<210> SEQ ID NO 12
<211> LENGTH: 21
<212> TYPE: PRT
<213> ORGANISM: Homo sapiens
<220> FEATURE:
<223> OTHER INFORMATION: Fragment peptide from bone sialoprotein (BSP).

<400> SEQUENCE: 12

Tyr Glu Ser Glu Asn Gly Glu Pro Arg Gly Asp Asn Tyr Arg Ala Tyr
 1               5                  10                  15

Glu Asp Glu Tyr Ser
             20

<210> SEQ ID NO 13
<211> LENGTH: 20
<212> TYPE: PRT
<213> ORGANISM: Homo sapiens
<220> FEATURE:
<223> OTHER INFORMATION: Fragment peptide from bone sialoprotein (BSP).

<400> SEQUENCE: 13

Tyr Glu Ser Glu Asn Gly Glu Pro Arg Gly Asp Asn Tyr Arg Ala Tyr
 1               5                  10                  15

Glu Asp Glu Tyr
             20

<210> SEQ ID NO 14
<211> LENGTH: 19
<212> TYPE: PRT
<213> ORGANISM: Homo sapiens
<220> FEATURE:
<223> OTHER INFORMATION: Fragment peptide from bone sialoprotein (BSP).
```

```
<400> SEQUENCE: 14

Tyr Glu Ser Glu Asn Gly Glu Pro Arg Gly Asp Asn Tyr Arg Ala Tyr
 1               5                  10                  15
Glu Asp Glu

<210> SEQ ID NO 15
<211> LENGTH: 18
<212> TYPE: PRT
<213> ORGANISM: Homo sapiens
<220> FEATURE:
<223> OTHER INFORMATION: Fragment peptide from bone sialoprotein (BSP).

<400> SEQUENCE: 15

Tyr Glu Ser Glu Asn Gly Glu Pro Arg Gly Asp Asn Tyr Arg Ala Tyr
 1               5                  10                  15
Glu Asp

<210> SEQ ID NO 16
<211> LENGTH: 17
<212> TYPE: PRT
<213> ORGANISM: Homo sapiens
<220> FEATURE:
<223> OTHER INFORMATION: Fragment peptide from bone sialoprotein (BSP).

<400> SEQUENCE: 16

Tyr Glu Ser Glu Asn Gly Glu Pro Arg Gly Asp Asn Tyr Arg Ala Tyr
 1               5                  10                  15
Glu

<210> SEQ ID NO 17
<211> LENGTH: 15
<212> TYPE: PRT
<213> ORGANISM: Homo sapiens
<220> FEATURE:
<223> OTHER INFORMATION: Fragment peptide from bone sialoprotein (BSP).

<400> SEQUENCE: 17

Tyr Glu Ser Glu Asn Gly Glu Pro Arg Gly Asp Asn Tyr Arg Ala
 1               5                  10                  15

<210> SEQ ID NO 18
<211> LENGTH: 14
<212> TYPE: PRT
<213> ORGANISM: Homo sapiens
<220> FEATURE:
<223> OTHER INFORMATION: Fragment peptide from bone sialoprotein (BSP).

<400> SEQUENCE: 18

Tyr Glu Ser Glu Asn Gly Glu Pro Arg Gly Asp Asn Tyr Arg
 1               5                  10

<210> SEQ ID NO 19
<211> LENGTH: 13
<212> TYPE: PRT
<213> ORGANISM: Homo sapiens
<220> FEATURE:
<223> OTHER INFORMATION: Fragment peptide from bone sialoprotein (BSP).

<400> SEQUENCE: 19

Tyr Glu Ser Glu Asn Gly Glu Pro Arg Gly Asp Asn Tyr
 1               5                  10
```

```
<210> SEQ ID NO 20
<211> LENGTH: 12
<212> TYPE: PRT
<213> ORGANISM: Homo sapiens
<220> FEATURE:
<223> OTHER INFORMATION: Fragment peptide from bone sialoprotein (BSP).

<400> SEQUENCE: 20

Tyr Glu Ser Glu Asn Gly Glu Pro Arg Gly Asp Asn
  1               5                  10

<210> SEQ ID NO 21
<211> LENGTH: 11
<212> TYPE: PRT
<213> ORGANISM: Homo sapiens
<220> FEATURE:
<223> OTHER INFORMATION: Fragment peptide from bone sialoprotein (BSP).

<400> SEQUENCE: 21

Tyr Glu Ser Glu Asn Gly Glu Pro Arg Gly Asp
  1               5                  10

<210> SEQ ID NO 22
<211> LENGTH: 24
<212> TYPE: PRT
<213> ORGANISM: Homo sapiens
<220> FEATURE:
<223> OTHER INFORMATION: Fragment peptide from bone sialoprotein (BSP).

<400> SEQUENCE: 22

Glu Ser Glu Asn Gly Glu Pro Arg Gly Asp Asn Tyr Arg Ala Tyr Glu
  1               5                  10                  15

Asp Glu Tyr Ser Tyr Phe Lys Gly
             20

<210> SEQ ID NO 23
<211> LENGTH: 23
<212> TYPE: PRT
<213> ORGANISM: Homo sapiens
<220> FEATURE:
<223> OTHER INFORMATION: Fragment peptide from bone sialoprotein (BSP).

<400> SEQUENCE: 23

Glu Ser Glu Asn Gly Glu Pro Arg Gly Asp Asn Tyr Arg Ala Tyr Glu
  1               5                  10                  15

Asp Glu Tyr Ser Tyr Phe Lys
             20

<210> SEQ ID NO 24
<211> LENGTH: 22
<212> TYPE: PRT
<213> ORGANISM: Homo sapiens
<220> FEATURE:
<223> OTHER INFORMATION: Fragment peptide from bone sialoprotein (BSP).

<400> SEQUENCE: 24

Glu Ser Glu Asn Gly Glu Pro Arg Gly Asp Asn Tyr Arg Ala Tyr Glu
  1               5                  10                  15

Asp Glu Tyr Ser Tyr Phe
             20

<210> SEQ ID NO 25
<211> LENGTH: 21
<212> TYPE: PRT
<213> ORGANISM: Homo sapiens
<220> FEATURE:
```

<223> OTHER INFORMATION: Fragment peptide from bone sialoprotein (BSP).

<400> SEQUENCE: 25

Glu Ser Glu Asn Gly Glu Pro Arg Gly Asp Asn Tyr Arg Ala Tyr Glu
1               5                   10                  15

Asp Glu Tyr Ser Tyr
            20

<210> SEQ ID NO 26
<211> LENGTH: 20
<212> TYPE: PRT
<213> ORGANISM: Homo sapiens
<220> FEATURE:
<223> OTHER INFORMATION: Fragment peptide from bone sialoprotein (BSP).

<400> SEQUENCE: 26

Glu Ser Glu Asn Gly Glu Pro Arg Gly Asp Asn Tyr Arg Ala Tyr Glu
1               5                   10                  15

Asp Glu Tyr Ser
            20

<210> SEQ ID NO 27
<211> LENGTH: 19
<212> TYPE: PRT
<213> ORGANISM: Homo sapiens
<220> FEATURE:
<223> OTHER INFORMATION: Fragment peptide from bone sialoprotein (BSP).

<400> SEQUENCE: 27

Glu Ser Glu Asn Gly Glu Pro Arg Gly Asp Asn Tyr Arg Ala Tyr Glu
1               5                   10                  15

Asp Glu Tyr

<210> SEQ ID NO 28
<211> LENGTH: 18
<212> TYPE: PRT
<213> ORGANISM: Homo sapiens
<220> FEATURE:
<223> OTHER INFORMATION: Fragment peptide from bone sialoprotein (BSP).

<400> SEQUENCE: 28

Glu Ser Glu Asn Gly Glu Pro Arg Gly Asp Asn Tyr Arg Ala Tyr Glu
1               5                   10                  15

Asp Glu

<210> SEQ ID NO 29
<211> LENGTH: 17
<212> TYPE: PRT
<213> ORGANISM: Homo sapiens
<220> FEATURE:
<223> OTHER INFORMATION: Fragment peptide from bone sialoprotein (BSP).

<400> SEQUENCE: 29

Glu Ser Glu Asn Gly Glu Pro Arg Gly Asp Asn Tyr Arg Ala Tyr Glu
1               5                   10                  15

Asp

<210> SEQ ID NO 30
<211> LENGTH: 16
<212> TYPE: PRT
<213> ORGANISM: Homo sapiens
<220> FEATURE:
<223> OTHER INFORMATION: Fragment peptide from bone sialoprotein (BSP).

```
<400> SEQUENCE: 30

Glu Ser Glu Asn Gly Glu Pro Arg Gly Asp Asn Tyr Arg Ala Tyr Glu
 1               5                  10                  15

<210> SEQ ID NO 31
<211> LENGTH: 15
<212> TYPE: PRT
<213> ORGANISM: Homo sapiens
<220> FEATURE:
<223> OTHER INFORMATION: Fragment peptide from bone sialoprotein (BSP).

<400> SEQUENCE: 31

Glu Ser Glu Asn Gly Glu Pro Arg Gly Asp Asn Tyr Arg Ala Tyr
 1               5                  10                  15

<210> SEQ ID NO 32
<211> LENGTH: 14
<212> TYPE: PRT
<213> ORGANISM: Homo sapiens
<220> FEATURE:
<223> OTHER INFORMATION: Fragment peptide from bone sialoprotein (BSP).

<400> SEQUENCE: 32

Glu Ser Glu Asn Gly Glu Pro Arg Gly Asp Asn Tyr Arg Ala
 1               5                  10

<210> SEQ ID NO 33
<211> LENGTH: 13
<212> TYPE: PRT
<213> ORGANISM: Homo sapiens
<220> FEATURE:
<223> OTHER INFORMATION: Fragment peptide from bone sialoprotein (BSP).

<400> SEQUENCE: 33

Glu Ser Glu Asn Gly Glu Pro Arg Gly Asp Asn Tyr Arg
 1               5                  10

<210> SEQ ID NO 34
<211> LENGTH: 12
<212> TYPE: PRT
<213> ORGANISM: Homo sapiens
<220> FEATURE:
<223> OTHER INFORMATION: Fragment peptide from bone sialoprotein (BSP).

<400> SEQUENCE: 34

Glu Ser Glu Asn Gly Glu Pro Arg Gly Asp Asn Tyr
 1               5                  10

<210> SEQ ID NO 35
<211> LENGTH: 11
<212> TYPE: PRT
<213> ORGANISM: Homo sapiens
<220> FEATURE:
<223> OTHER INFORMATION: Fragment peptide from bone sialoprotein (BSP).

<400> SEQUENCE: 35

Glu Ser Glu Asn Gly Glu Pro Arg Gly Asp Asn
 1               5                  10

<210> SEQ ID NO 36
<211> LENGTH: 10
<212> TYPE: PRT
<213> ORGANISM: Homo sapiens
<220> FEATURE:
<223> OTHER INFORMATION: Fragment peptide from bone sialoprotein (BSP).
```

<400> SEQUENCE: 36

Glu Ser Glu Asn Gly Glu Pro Arg Gly Asp
 1               5                  10

<210> SEQ ID NO 37
<211> LENGTH: 23
<212> TYPE: PRT
<213> ORGANISM: Homo sapiens
<220> FEATURE:
<223> OTHER INFORMATION: Fragment peptide from bone sialoprotein (BSP).

<400> SEQUENCE: 37

Ser Glu Asn Gly Glu Pro Arg Gly Asp Asn Tyr Arg Ala Tyr Glu Asp
 1               5                  10                  15

Glu Tyr Ser Tyr Phe Lys Gly
            20

<210> SEQ ID NO 38
<211> LENGTH: 22
<212> TYPE: PRT
<213> ORGANISM: Homo sapiens
<220> FEATURE:
<223> OTHER INFORMATION: Fragment peptide from bone sialoprotein (BSP).

<400> SEQUENCE: 38

Ser Glu Asn Gly Glu Pro Arg Gly Asp Asn Tyr Arg Ala Tyr Glu Asp
 1               5                  10                  15

Glu Tyr Ser Tyr Phe Lys
            20

<210> SEQ ID NO 39
<211> LENGTH: 21
<212> TYPE: PRT
<213> ORGANISM: Homo sapiens
<220> FEATURE:
<223> OTHER INFORMATION: Fragment peptide from bone sialoprotein (BSP).

<400> SEQUENCE: 39

Ser Glu Asn Gly Glu Pro Arg Gly Asp Asn Tyr Arg Ala Tyr Glu Asp
 1               5                  10                  15

Glu Tyr Ser Tyr Phe
            20

<210> SEQ ID NO 40
<211> LENGTH: 20
<212> TYPE: PRT
<213> ORGANISM: Homo sapiens
<220> FEATURE:
<223> OTHER INFORMATION: Fragment peptide from bone sialoprotein (BSP).

<400> SEQUENCE: 40

Ser Glu Asn Gly Glu Pro Arg Gly Asp Asn Tyr Arg Ala Tyr Glu Asp
 1               5                  10                  15

Glu Tyr Ser Tyr
            20

<210> SEQ ID NO 41
<211> LENGTH: 19
<212> TYPE: PRT
<213> ORGANISM: Homo sapiens
<220> FEATURE:
<223> OTHER INFORMATION: Fragment peptide from bone sialoprotein (BSP).

```
<400> SEQUENCE: 41

Ser Glu Asn Gly Glu Pro Arg Gly Asp Asn Tyr Arg Ala Tyr Glu Asp
 1               5                  10                  15
Glu Tyr Ser

<210> SEQ ID NO 42
<211> LENGTH: 18
<212> TYPE: PRT
<213> ORGANISM: Homo sapiens
<220> FEATURE:
<223> OTHER INFORMATION: Fragment peptide from bone sialoprotein (BSP).

<400> SEQUENCE: 42

Ser Glu Asn Gly Glu Pro Arg Gly Asp Asn Tyr Arg Ala Tyr Glu Asp
 1               5                  10                  15
Glu Tyr

<210> SEQ ID NO 43
<211> LENGTH: 17
<212> TYPE: PRT
<213> ORGANISM: Homo sapiens
<220> FEATURE:
<223> OTHER INFORMATION: Fragment peptide from bone sialoprotein (BSP).

<400> SEQUENCE: 43

Ser Glu Asn Gly Glu Pro Arg Gly Asp Asn Tyr Arg Ala Tyr Glu Asp
 1               5                  10                  15
Glu

<210> SEQ ID NO 44
<211> LENGTH: 16
<212> TYPE: PRT
<213> ORGANISM: Homo sapiens
<220> FEATURE:
<223> OTHER INFORMATION: Fragment peptide from bone sialoprotein (BSP).

<400> SEQUENCE: 44

Ser Glu Asn Gly Glu Pro Arg Gly Asp Asn Tyr Arg Ala Tyr Glu Asp
 1               5                  10                  15

<210> SEQ ID NO 45
<211> LENGTH: 15
<212> TYPE: PRT
<213> ORGANISM: Homo sapiens
<220> FEATURE:
<223> OTHER INFORMATION: Fragment peptide from bone sialoprotein (BSP).

<400> SEQUENCE: 45

Ser Glu Asn Gly Glu Pro Arg Gly Asp Asn Tyr Arg Ala Tyr Glu
 1               5                  10                  15

<210> SEQ ID NO 46
<211> LENGTH: 14
<212> TYPE: PRT
<213> ORGANISM: Homo sapiens
<220> FEATURE:
<223> OTHER INFORMATION: Fragment peptide from bone sialoprotein (BSP).

<400> SEQUENCE: 46

Ser Glu Asn Gly Glu Pro Arg Gly Asp Asn Tyr Arg Ala Tyr
 1               5                  10
```

```
<210> SEQ ID NO 47
<211> LENGTH: 13
<212> TYPE: PRT
<213> ORGANISM: Homo sapiens
<220> FEATURE:
<223> OTHER INFORMATION: Fragment peptide from bone sialoprotein (BSP).

<400> SEQUENCE: 47

Ser Glu Asn Gly Glu Pro Arg Gly Asp Asn Tyr Arg Ala
 1               5                  10

<210> SEQ ID NO 48
<211> LENGTH: 12
<212> TYPE: PRT
<213> ORGANISM: Homo sapiens
<220> FEATURE:
<223> OTHER INFORMATION: Fragment peptide from bone sialoprotein (BSP).

<400> SEQUENCE: 48

Ser Glu Asn Gly Glu Pro Arg Gly Asp Asn Tyr Arg
 1               5                  10

<210> SEQ ID NO 49
<211> LENGTH: 11
<212> TYPE: PRT
<213> ORGANISM: Homo sapiens
<220> FEATURE:
<223> OTHER INFORMATION: Fragment peptide from bone sialoprotein (BSP).

<400> SEQUENCE: 49

Ser Glu Asn Gly Glu Pro Arg Gly Asp Asn Tyr
 1               5                  10

<210> SEQ ID NO 50
<211> LENGTH: 10
<212> TYPE: PRT
<213> ORGANISM: Homo sapiens
<220> FEATURE:
<223> OTHER INFORMATION: Fragment peptide from bone sialoprotein (BSP).

<400> SEQUENCE: 50

Ser Glu Asn Gly Glu Pro Arg Gly Asp Asn
 1               5                  10

<210> SEQ ID NO 51
<211> LENGTH: 9
<212> TYPE: PRT
<213> ORGANISM: Homo sapiens
<220> FEATURE:
<223> OTHER INFORMATION: Fragment peptide from bone sialoprotein (BSP).

<400> SEQUENCE: 51

Ser Glu Asn Gly Glu Pro Arg Gly Asp
 1               5

<210> SEQ ID NO 52
<211> LENGTH: 22
<212> TYPE: PRT
<213> ORGANISM: Homo sapiens
<220> FEATURE:
<223> OTHER INFORMATION: Fragment peptide from bone sialoprotein (BSP).

<400> SEQUENCE: 52

Glu Asn Gly Glu Pro Arg Gly Asp Asn Tyr Arg Ala Tyr Glu Asp Glu
 1               5                  10                  15

Tyr Ser Tyr Phe Lys Gly
            20
```

<210> SEQ ID NO 53
<211> LENGTH: 21
<212> TYPE: PRT
<213> ORGANISM: Homo sapiens
<220> FEATURE:
<223> OTHER INFORMATION: Fragment peptide from bone sialoprotein (BSP).

<400> SEQUENCE: 53

Glu Asn Gly Glu Pro Arg Gly Asp Asn Tyr Arg Ala Tyr Glu Asp Glu
 1               5                  10                  15

Tyr Ser Tyr Phe Lys
            20

<210> SEQ ID NO 54
<211> LENGTH: 20
<212> TYPE: PRT
<213> ORGANISM: Homo sapiens
<220> FEATURE:
<223> OTHER INFORMATION: Fragment peptide from bone sialoprotein (BSP).

<400> SEQUENCE: 54

Glu Asn Gly Glu Pro Arg Gly Asp Asn Tyr Arg Ala Tyr Glu Asp Glu
 1               5                  10                  15

Tyr Ser Tyr Phe
            20

<210> SEQ ID NO 55
<211> LENGTH: 19
<212> TYPE: PRT
<213> ORGANISM: Homo sapiens
<220> FEATURE:
<223> OTHER INFORMATION: Fragment peptide from bone sialoprotein (BSP).

<400> SEQUENCE: 55

Glu Asn Gly Glu Pro Arg Gly Asp Asn Tyr Arg Ala Tyr Glu Asp Glu
 1               5                  10                  15

Tyr Ser Tyr

<210> SEQ ID NO 56
<211> LENGTH: 18
<212> TYPE: PRT
<213> ORGANISM: Homo sapiens
<220> FEATURE:
<223> OTHER INFORMATION: Fragment peptide from bone sialoprotein (BSP).

<400> SEQUENCE: 56

Glu Asn Gly Glu Pro Arg Gly Asp Asn Tyr Arg Ala Tyr Glu Asp Glu
 1               5                  10                  15

Tyr Ser

<210> SEQ ID NO 57
<211> LENGTH: 17
<212> TYPE: PRT
<213> ORGANISM: Homo sapiens
<220> FEATURE:
<223> OTHER INFORMATION: Fragment peptide from bone sialoprotein (BSP).

<400> SEQUENCE: 57

Glu Asn Gly Glu Pro Arg Gly Asp Asn Tyr Arg Ala Tyr Glu Asp Glu
 1               5                  10                  15

Tyr

```
<210> SEQ ID NO 58
<211> LENGTH: 16
<212> TYPE: PRT
<213> ORGANISM: Homo sapiens
<220> FEATURE:
<223> OTHER INFORMATION: Fragment peptide from bone sialoprotein (BSP).

<400> SEQUENCE: 58

Glu Asn Gly Glu Pro Arg Gly Asp Asn Tyr Arg Ala Tyr Glu Asp Glu
 1               5                  10                  15

<210> SEQ ID NO 59
<211> LENGTH: 15
<212> TYPE: PRT
<213> ORGANISM: Homo sapiens
<220> FEATURE:
<223> OTHER INFORMATION: Fragment peptide from bone sialoprotein (BSP).

<400> SEQUENCE: 59

Glu Asn Gly Glu Pro Arg Gly Asp Asn Tyr Arg Ala Tyr Glu Asp
 1               5                  10                  15

<210> SEQ ID NO 60
<211> LENGTH: 14
<212> TYPE: PRT
<213> ORGANISM: Homo sapiens
<220> FEATURE:
<223> OTHER INFORMATION: Fragment peptide from bone sialoprotein (BSP).

<400> SEQUENCE: 60

Glu Asn Gly Glu Pro Arg Gly Asp Asn Tyr Arg Ala Tyr Glu
 1               5                  10

<210> SEQ ID NO 61
<211> LENGTH: 13
<212> TYPE: PRT
<213> ORGANISM: Homo sapiens
<220> FEATURE:
<223> OTHER INFORMATION: Fragment peptide from bone sialoprotein (BSP).

<400> SEQUENCE: 61

Glu Asn Gly Glu Pro Arg Gly Asp Asn Tyr Arg Ala Tyr
 1               5                  10

<210> SEQ ID NO 62
<211> LENGTH: 12
<212> TYPE: PRT
<213> ORGANISM: Homo sapiens
<220> FEATURE:
<223> OTHER INFORMATION: Fragment peptide from bone sialoprotein (BSP).

<400> SEQUENCE: 62

Glu Asn Gly Glu Pro Arg Gly Asp Asn Tyr Arg Ala
 1               5                  10

<210> SEQ ID NO 63
<211> LENGTH: 11
<212> TYPE: PRT
<213> ORGANISM: Homo sapiens
<220> FEATURE:
<223> OTHER INFORMATION: Fragment peptide from bone sialoprotein (BSP).

<400> SEQUENCE: 63

Glu Asn Gly Glu Pro Arg Gly Asp Asn Tyr Arg
 1               5                  10
```

```
<210> SEQ ID NO 64
<211> LENGTH: 9
<212> TYPE: PRT
<213> ORGANISM: Homo sapiens
<220> FEATURE:
<223> OTHER INFORMATION: Fragment peptide from bone sialoprotein (BSP).

<400> SEQUENCE: 64

Glu Asn Gly Glu Pro Arg Gly Asp Asn
 1               5

<210> SEQ ID NO 65
<211> LENGTH: 8
<212> TYPE: PRT
<213> ORGANISM: Homo sapiens
<220> FEATURE:
<223> OTHER INFORMATION: Fragment peptide from bone sialoprotein (BSP).

<400> SEQUENCE: 65

Glu Asn Gly Glu Pro Arg Gly Asp
 1               5

<210> SEQ ID NO 66
<211> LENGTH: 21
<212> TYPE: PRT
<213> ORGANISM: Homo sapiens
<220> FEATURE:
<223> OTHER INFORMATION: Fragment peptide from bone sialoprotein (BSP).

<400> SEQUENCE: 66

Asn Gly Glu Pro Arg Gly Asp Asn Tyr Arg Ala Tyr Glu Asp Glu Tyr
 1               5                  10                  15

Ser Tyr Phe Lys Gly
            20

<210> SEQ ID NO 67
<211> LENGTH: 20
<212> TYPE: PRT
<213> ORGANISM: Homo sapiens
<220> FEATURE:
<223> OTHER INFORMATION: Fragment peptide from bone sialoprotein (BSP).

<400> SEQUENCE: 67

Asn Gly Glu Pro Arg Gly Asp Asn Tyr Arg Ala Tyr Glu Asp Glu Tyr
 1               5                  10                  15

Ser Tyr Phe Lys
            20

<210> SEQ ID NO 68
<211> LENGTH: 19
<212> TYPE: PRT
<213> ORGANISM: Homo sapiens
<220> FEATURE:
<223> OTHER INFORMATION: Fragment peptide from bone sialoprotein (BSP).

<400> SEQUENCE: 68

Asn Gly Glu Pro Arg Gly Asp Asn Tyr Arg Ala Tyr Glu Asp Glu Tyr
 1               5                  10                  15

Ser Tyr Phe

<210> SEQ ID NO 69
<211> LENGTH: 18
<212> TYPE: PRT
<213> ORGANISM: Homo sapiens
<220> FEATURE:
<223> OTHER INFORMATION: Fragment peptide from bone sialoprotein (BSP).
```

```
<400> SEQUENCE: 69

Asn Gly Glu Pro Arg Gly Asp Asn Tyr Arg Ala Tyr Glu Asp Glu Tyr
 1               5                  10                  15
Ser Tyr

<210> SEQ ID NO 70
<211> LENGTH: 17
<212> TYPE: PRT
<213> ORGANISM: Homo sapiens
<220> FEATURE:
<223> OTHER INFORMATION: Fragment peptide from bone sialoprotein (BSP).

<400> SEQUENCE: 70

Asn Gly Glu Pro Arg Gly Asp Asn Tyr Arg Ala Tyr Glu Asp Glu Tyr
 1               5                  10                  15
Ser

<210> SEQ ID NO 71
<211> LENGTH: 16
<212> TYPE: PRT
<213> ORGANISM: Homo sapiens
<220> FEATURE:
<223> OTHER INFORMATION: Fragment peptide from bone sialoprotein (BSP).

<400> SEQUENCE: 71

Asn Gly Glu Pro Arg Gly Asp Asn Tyr Arg Ala Tyr Glu Asp Glu Tyr
 1               5                  10                  15

<210> SEQ ID NO 72
<211> LENGTH: 15
<212> TYPE: PRT
<213> ORGANISM: Homo sapiens
<220> FEATURE:
<223> OTHER INFORMATION: Fragment peptide from bone sialoprotein (BSP).

<400> SEQUENCE: 72

Asn Gly Glu Pro Arg Gly Asp Asn Tyr Arg Ala Tyr Glu Asp Glu
 1               5                  10                  15

<210> SEQ ID NO 73
<211> LENGTH: 14
<212> TYPE: PRT
<213> ORGANISM: Homo sapiens
<220> FEATURE:
<223> OTHER INFORMATION: Fragment peptide from bone sialoprotein (BSP).

<400> SEQUENCE: 73

Asn Gly Glu Pro Arg Gly Asp Asn Tyr Arg Ala Tyr Glu Asp
 1               5                  10

<210> SEQ ID NO 74
<211> LENGTH: 13
<212> TYPE: PRT
<213> ORGANISM: Homo sapiens
<220> FEATURE:
<223> OTHER INFORMATION: Fragment peptide from bone sialoprotein (BSP).

<400> SEQUENCE: 74

Asn Gly Glu Pro Arg Gly Asp Asn Tyr Arg Ala Tyr Glu
 1               5                  10

<210> SEQ ID NO 75
<211> LENGTH: 12
<212> TYPE: PRT
<213> ORGANISM: Homo sapiens
```

```
<220> FEATURE:
<223> OTHER INFORMATION: Fragment peptide from bone sialoprotein (BSP).

<400> SEQUENCE: 75

Asn Gly Glu Pro Arg Gly Asp Asn Tyr Arg Ala Tyr
 1               5                  10

<210> SEQ ID NO 76
<211> LENGTH: 11
<212> TYPE: PRT
<213> ORGANISM: Homo sapiens
<220> FEATURE:
<223> OTHER INFORMATION: Fragment peptide from bone sialoprotein (BSP).

<400> SEQUENCE: 76

Asn Gly Glu Pro Arg Gly Asp Asn Tyr Arg Ala
 1               5                  10

<210> SEQ ID NO 77
<211> LENGTH: 10
<212> TYPE: PRT
<213> ORGANISM: Homo sapiens
<220> FEATURE:
<223> OTHER INFORMATION: Fragment peptide from bone sialoprotein (BSP).

<400> SEQUENCE: 77

Asn Gly Glu Pro Arg Gly Asp Asn Tyr Arg
 1               5                  10

<210> SEQ ID NO 78
<211> LENGTH: 9
<212> TYPE: PRT
<213> ORGANISM: Homo sapiens
<220> FEATURE:
<223> OTHER INFORMATION: Fragment peptide from bone sialoprotein (BSP).

<400> SEQUENCE: 78

Asn Gly Glu Pro Arg Gly Asp Asn Tyr
 1               5

<210> SEQ ID NO 79
<211> LENGTH: 8
<212> TYPE: PRT
<213> ORGANISM: Homo sapiens
<220> FEATURE:
<223> OTHER INFORMATION: Fragment peptide from bone sialoprotein (BSP).

<400> SEQUENCE: 79

Asn Gly Glu Pro Arg Gly Asp Asn
 1               5

<210> SEQ ID NO 80
<211> LENGTH: 7
<212> TYPE: PRT
<213> ORGANISM: Homo sapiens
<220> FEATURE:
<223> OTHER INFORMATION: Fragment peptide from bone sialoprotein (BSP).

<400> SEQUENCE: 80

Asn Gly Glu Pro Arg Gly Asp
 1               5

<210> SEQ ID NO 81
<211> LENGTH: 20
<212> TYPE: PRT
<213> ORGANISM: Homo sapiens
<220> FEATURE:
```

<223> OTHER INFORMATION: Fragment peptide from bone sialoprotein (BSP).

<400> SEQUENCE: 81

Gly Glu Pro Arg Gly Asp Asn Tyr Arg Ala Tyr Glu Asp Glu Tyr Ser
 1               5                  10                  15

Tyr Phe Lys Gly
            20

<210> SEQ ID NO 82
<211> LENGTH: 19
<212> TYPE: PRT
<213> ORGANISM: Homo sapiens
<220> FEATURE:
<223> OTHER INFORMATION: Fragment peptide from bone sialoprotein (BSP).

<400> SEQUENCE: 82

Gly Glu Pro Arg Gly Asp Asn Tyr Arg Ala Tyr Glu Asp Glu Tyr Ser
 1               5                  10                  15

Tyr Phe Lys

<210> SEQ ID NO 83
<211> LENGTH: 18
<212> TYPE: PRT
<213> ORGANISM: Homo sapiens
<220> FEATURE:
<223> OTHER INFORMATION: Fragment peptide from bone sialoprotein (BSP).

<400> SEQUENCE: 83

Gly Glu Pro Arg Gly Asp Asn Tyr Arg Ala Tyr Glu Asp Glu Tyr Ser
 1               5                  10                  15

Tyr Phe

<210> SEQ ID NO 84
<211> LENGTH: 17
<212> TYPE: PRT
<213> ORGANISM: Homo sapiens
<220> FEATURE:
<223> OTHER INFORMATION: Fragment peptide from bone sialoprotein (BSP).

<400> SEQUENCE: 84

Gly Glu Pro Arg Gly Asp Asn Tyr Arg Ala Tyr Glu Asp Glu Tyr Ser
 1               5                  10                  15

Tyr

<210> SEQ ID NO 85
<211> LENGTH: 16
<212> TYPE: PRT
<213> ORGANISM: Homo sapiens
<220> FEATURE:
<223> OTHER INFORMATION: Fragment peptide from bone sialoprotein (BSP).

<400> SEQUENCE: 85

Gly Glu Pro Arg Gly Asp Asn Tyr Arg Ala Tyr Glu Asp Glu Tyr Ser
 1               5                  10                  15

<210> SEQ ID NO 86
<211> LENGTH: 15
<212> TYPE: PRT
<213> ORGANISM: Homo sapiens
<220> FEATURE:
<223> OTHER INFORMATION: Fragment peptide from bone sialoprotein (BSP).

```
<400> SEQUENCE: 86

Gly Glu Pro Arg Gly Asp Asn Tyr Arg Ala Tyr Glu Asp Glu Tyr
 1               5                  10                  15

<210> SEQ ID NO 87
<211> LENGTH: 14
<212> TYPE: PRT
<213> ORGANISM: Homo sapiens
<220> FEATURE:
<223> OTHER INFORMATION: Fragment peptide from bone sialoprotein (BSP).

<400> SEQUENCE: 87

Gly Glu Pro Arg Gly Asp Asn Tyr Arg Ala Tyr Glu Asp Glu
 1               5                  10

<210> SEQ ID NO 88
<211> LENGTH: 13
<212> TYPE: PRT
<213> ORGANISM: Homo sapiens
<220> FEATURE:
<223> OTHER INFORMATION: Fragment peptide from bone sialoprotein (BSP).

<400> SEQUENCE: 88

Gly Glu Pro Arg Gly Asp Asn Tyr Arg Ala Tyr Glu Asp
 1               5                  10

<210> SEQ ID NO 89
<211> LENGTH: 12
<212> TYPE: PRT
<213> ORGANISM: Homo sapiens
<220> FEATURE:
<223> OTHER INFORMATION: Fragment peptide from bone sialoprotein (BSP).

<400> SEQUENCE: 89

Gly Glu Pro Arg Gly Asp Asn Tyr Arg Ala Tyr Glu
 1               5                  10

<210> SEQ ID NO 90
<211> LENGTH: 11
<212> TYPE: PRT
<213> ORGANISM: Homo sapiens
<220> FEATURE:
<223> OTHER INFORMATION: Fragment peptide from bone sialoprotein (BSP).

<400> SEQUENCE: 90

Gly Glu Pro Arg Gly Asp Asn Tyr Arg Ala Tyr
 1               5                  10

<210> SEQ ID NO 91
<211> LENGTH: 10
<212> TYPE: PRT
<213> ORGANISM: Homo sapiens
<220> FEATURE:
<223> OTHER INFORMATION: Fragment peptide from bone sialoprotein (BSP).

<400> SEQUENCE: 91

Gly Glu Pro Arg Gly Asp Asn Tyr Arg Ala
 1               5                  10

<210> SEQ ID NO 92
<211> LENGTH: 9
<212> TYPE: PRT
<213> ORGANISM: Homo sapiens
<220> FEATURE:
<223> OTHER INFORMATION: Fragment peptide from bone sialoprotein (BSP).
```

```
<400> SEQUENCE: 92

Gly Glu Pro Arg Gly Asp Asn Tyr Arg
 1               5

<210> SEQ ID NO 93
<211> LENGTH: 8
<212> TYPE: PRT
<213> ORGANISM: Homo sapiens
<220> FEATURE:
<223> OTHER INFORMATION: Fragment peptide from bone sialoprotein (BSP).

<400> SEQUENCE: 93

Gly Glu Pro Arg Gly Asp Asn Tyr
 1               5

<210> SEQ ID NO 94
<211> LENGTH: 7
<212> TYPE: PRT
<213> ORGANISM: Homo sapiens
<220> FEATURE:
<223> OTHER INFORMATION: Fragment peptide from bone sialoprotein (BSP).

<400> SEQUENCE: 94

Gly Glu Pro Arg Gly Asp Asn
 1               5

<210> SEQ ID NO 95
<211> LENGTH: 24
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 95

Tyr Glu Ser Glu Asn Gly Glu Pro Arg Gly Asp Asn Tyr Arg Ala Tyr
 1               5                  10                  15

Glu Asp Glu Tyr Ser Tyr Phe Lys
            20

<210> SEQ ID NO 96
<211> LENGTH: 23
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 96

Tyr Glu Ser Glu Asn Gly Glu Pro Arg Gly Asp Asn Tyr Arg Ala Tyr
 1               5                  10                  15

Glu Asp Glu Tyr Ser Tyr Phe
            20

<210> SEQ ID NO 97
<211> LENGTH: 22
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 97

Tyr Glu Ser Glu Asn Gly Glu Pro Arg Gly Asp Asn Tyr Arg Ala Tyr
 1               5                  10                  15
```

```
Glu Asp Glu Tyr Ser Tyr
            20
```

```
<210> SEQ ID NO 98
<211> LENGTH: 21
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 98
```

```
Tyr Glu Ser Glu Asn Gly Glu Pro Arg Gly Asp Asn Tyr Arg Ala Tyr
 1               5                  10                  15

Glu Asp Glu Tyr Ser
            20
```

```
<210> SEQ ID NO 99
<211> LENGTH: 20
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 99
```

```
Tyr Glu Ser Glu Asn Gly Glu Pro Arg Gly Asp Asn Tyr Arg Ala Tyr
 1               5                  10                  15

Glu Asp Glu Tyr
            20
```

```
<210> SEQ ID NO 100
<211> LENGTH: 19
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 100
```

```
Tyr Glu Ser Glu Asn Gly Glu Pro Arg Gly Asp Asn Tyr Arg Ala Tyr
 1               5                  10                  15

Glu Asp Glu
```

```
<210> SEQ ID NO 101
<211> LENGTH: 18
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 101
```

```
Tyr Glu Ser Glu Asn Gly Glu Pro Arg Gly Asp Asn Tyr Arg Ala Tyr
 1               5                  10                  15

Glu Asp
```

```
<210> SEQ ID NO 102
<211> LENGTH: 17
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.
```

-continued

<400> SEQUENCE: 102

Tyr Glu Ser Glu Asn Gly Glu Pro Arg Gly Asp Asn Tyr Arg Ala Tyr
1               5                   10                  15
Glu

<210> SEQ ID NO 103
<211> LENGTH: 15
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 103

Tyr Glu Ser Glu Asn Gly Glu Pro Arg Gly Asp Asn Tyr Arg Ala
1               5                   10                  15

<210> SEQ ID NO 104
<211> LENGTH: 14
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 104

Tyr Glu Ser Glu Asn Gly Glu Pro Arg Gly Asp Asn Tyr Arg
1               5                   10

<210> SEQ ID NO 105
<211> LENGTH: 13
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 105

Tyr Glu Ser Glu Asn Gly Glu Pro Arg Gly Asp Asn Tyr
1               5                   10

<210> SEQ ID NO 106
<211> LENGTH: 12
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 106

Tyr Glu Ser Glu Asn Gly Glu Pro Arg Gly Asp Asn
1               5                   10

<210> SEQ ID NO 107
<211> LENGTH: 11
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 107

Tyr Glu Ser Glu Asn Gly Glu Pro Arg Gly Asp
1               5                   10

<210> SEQ ID NO 108
<211> LENGTH: 24
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 108

Glu Ser Glu Asn Gly Glu Pro Arg Gly Asp Asn Tyr Arg Ala Tyr Glu
 1               5                  10                  15

Asp Glu Tyr Ser Tyr Phe Lys Gly
            20

<210> SEQ ID NO 109
<211> LENGTH: 23
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 109

Glu Ser Glu Asn Gly Glu Pro Arg Gly Asp Asn Tyr Arg Ala Tyr Glu
 1               5                  10                  15

Asp Glu Tyr Ser Tyr Phe Lys
            20

<210> SEQ ID NO 110
<211> LENGTH: 22
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 110

Glu Ser Glu Asn Gly Glu Pro Arg Gly Asp Asn Tyr Arg Ala Tyr Glu
 1               5                  10                  15

Asp Glu Tyr Ser Tyr Phe
            20

<210> SEQ ID NO 111
<211> LENGTH: 21
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 111

Glu Ser Glu Asn Gly Glu Pro Arg Gly Asp Asn Tyr Arg Ala Tyr Glu
 1               5                  10                  15

Asp Glu Tyr Ser Tyr
            20

<210> SEQ ID NO 112
<211> LENGTH: 20
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 112

Glu Ser Glu Asn Gly Glu Pro Arg Gly Asp Asn Tyr Arg Ala Tyr Glu
 1               5                  10                  15

Asp Glu Tyr Ser
            20

<210> SEQ ID NO 113
<211> LENGTH: 19
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 113

Glu Ser Glu Asn Gly Glu Pro Arg Gly Asp Asn Tyr Arg Ala Tyr Glu
 1               5                  10                  15

Asp Glu Tyr

<210> SEQ ID NO 114
<211> LENGTH: 18
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 114

Glu Ser Glu Asn Gly Glu Pro Arg Gly Asp Asn Tyr Arg Ala Tyr Glu
 1               5                  10                  15

Asp Glu

<210> SEQ ID NO 115
<211> LENGTH: 17
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 115

Glu Ser Glu Asn Gly Glu Pro Arg Gly Asp Asn Tyr Arg Ala Tyr Glu
 1               5                  10                  15

Asp

<210> SEQ ID NO 116
<211> LENGTH: 16
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 116

Glu Ser Glu Asn Gly Glu Pro Arg Gly Asp Asn Tyr Arg Ala Tyr Glu
 1               5                  10                  15

<210> SEQ ID NO 117
<211> LENGTH: 15
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

```
<400> SEQUENCE: 117

Glu Ser Glu Asn Gly Glu Pro Arg Gly Asp Asn Tyr Arg Ala Tyr
 1               5                  10                  15

<210> SEQ ID NO 118
<211> LENGTH: 14
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 118

Glu Ser Glu Asn Gly Glu Pro Arg Gly Asp Asn Tyr Arg Ala
 1               5                  10

<210> SEQ ID NO 119
<211> LENGTH: 13
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 119

Glu Ser Glu Asn Gly Glu Pro Arg Gly Asp Asn Tyr Arg
 1               5                  10

<210> SEQ ID NO 120
<211> LENGTH: 12
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 120

Glu Ser Glu Asn Gly Glu Pro Arg Gly Asp Asn Tyr
 1               5                  10

<210> SEQ ID NO 121
<211> LENGTH: 11
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 121

Glu Ser Glu Asn Gly Glu Pro Arg Gly Asp Asn
 1               5                  10

<210> SEQ ID NO 122
<211> LENGTH: 10
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 122

Glu Ser Glu Asn Gly Glu Pro Arg Gly Asp
 1               5                  10

<210> SEQ ID NO 123
<211> LENGTH: 23
<212> TYPE: PRT
```

```
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 123

Ser Glu Asn Gly Glu Pro Arg Gly Asp Asn Tyr Arg Ala Tyr Glu Asp
 1               5                  10                  15

Glu Tyr Ser Tyr Phe Lys Gly
            20

<210> SEQ ID NO 124
<211> LENGTH: 22
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 124

Ser Glu Asn Gly Glu Pro Arg Gly Asp Asn Tyr Arg Ala Tyr Glu Asp
 1               5                  10                  15

Glu Tyr Ser Tyr Phe Lys
            20

<210> SEQ ID NO 125
<211> LENGTH: 21
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 125

Ser Glu Asn Gly Glu Pro Arg Gly Asp Asn Tyr Arg Ala Tyr Glu Asp
 1               5                  10                  15

Glu Tyr Ser Tyr Phe
            20

<210> SEQ ID NO 126
<211> LENGTH: 20
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 126

Ser Glu Asn Gly Glu Pro Arg Gly Asp Asn Tyr Arg Ala Tyr Glu Asp
 1               5                  10                  15

Glu Tyr Ser Tyr
            20

<210> SEQ ID NO 127
<211> LENGTH: 19
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 127

Ser Glu Asn Gly Glu Pro Arg Gly Asp Asn Tyr Arg Ala Tyr Glu Asp
 1               5                  10                  15

Glu Tyr Ser
```

```
<210> SEQ ID NO 128
<211> LENGTH: 18
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 128

Ser Glu Asn Gly Glu Pro Arg Gly Asp Asn Tyr Arg Ala Tyr Glu Asp
 1               5                  10                  15
Glu Tyr

<210> SEQ ID NO 129
<211> LENGTH: 17
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 129

Ser Glu Asn Gly Glu Pro Arg Gly Asp Asn Tyr Arg Ala Tyr Glu Asp
 1               5                  10                  15
Glu

<210> SEQ ID NO 130
<211> LENGTH: 16
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 130

Ser Glu Asn Gly Glu Pro Arg Gly Asp Asn Tyr Arg Ala Tyr Glu Asp
 1               5                  10                  15

<210> SEQ ID NO 131
<211> LENGTH: 15
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 131

Ser Glu Asn Gly Glu Pro Arg Gly Asp Asn Tyr Arg Ala Tyr Glu
 1               5                  10                  15

<210> SEQ ID NO 132
<211> LENGTH: 14
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 132

Ser Glu Asn Gly Glu Pro Arg Gly Asp Asn Tyr Arg Ala Tyr
 1               5                  10

<210> SEQ ID NO 133
<211> LENGTH: 13
<212> TYPE: PRT
```

```
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 133

Ser Glu Asn Gly Glu Pro Arg Gly Asp Asn Tyr Arg Ala
 1               5                  10

<210> SEQ ID NO 134
<211> LENGTH: 12
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 134

Ser Glu Asn Gly Glu Pro Arg Gly Asp Asn Tyr Arg
 1               5                  10

<210> SEQ ID NO 135
<211> LENGTH: 11
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 135

Ser Glu Asn Gly Glu Pro Arg Gly Asp Asn Tyr
 1               5                  10

<210> SEQ ID NO 136
<211> LENGTH: 10
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 136

Ser Glu Asn Gly Glu Pro Arg Gly Asp Asn
 1               5                  10

<210> SEQ ID NO 137
<211> LENGTH: 9
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 137

Ser Glu Asn Gly Glu Pro Arg Gly Asp
 1               5

<210> SEQ ID NO 138
<211> LENGTH: 22
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.
```

```
<400> SEQUENCE: 138

Glu Asn Gly Glu Pro Arg Gly Asp Asn Tyr Arg Ala Tyr Glu Asp Glu
 1               5                  10                  15

Tyr Ser Tyr Phe Lys Gly
            20

<210> SEQ ID NO 139
<211> LENGTH: 21
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 139

Glu Asn Gly Glu Pro Arg Gly Asp Asn Tyr Arg Ala Tyr Glu Asp Glu
 1               5                  10                  15

Tyr Ser Tyr Phe Lys
            20

<210> SEQ ID NO 140
<211> LENGTH: 20
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 140

Glu Asn Gly Glu Pro Arg Gly Asp Asn Tyr Arg Ala Tyr Glu Asp Glu
 1               5                  10                  15

Tyr Ser Tyr Phe
            20

<210> SEQ ID NO 141
<211> LENGTH: 19
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 141

Glu Asn Gly Glu Pro Arg Gly Asp Asn Tyr Arg Ala Tyr Glu Asp Glu
 1               5                  10                  15

Tyr Ser Tyr

<210> SEQ ID NO 142
<211> LENGTH: 18
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 142

Glu Asn Gly Glu Pro Arg Gly Asp Asn Tyr Arg Ala Tyr Glu Asp Glu
 1               5                  10                  15

Tyr Ser

<210> SEQ ID NO 143
<211> LENGTH: 17
<212> TYPE: PRT
<213> ORGANISM: Homo sapiens
```

```
<220> FEATURE:
<223> OTHER INFORMATION: Fragment peptide from bone sialoprotein (BSP).
<223> OTHER INFORMATION: The peptide has a C-terminal amide group.

<400> SEQUENCE: 143

Glu Asn Gly Glu Pro Arg Gly Asp Asn Tyr Arg Ala Tyr Glu Asp Glu
  1               5                  10                  15
Tyr

<210> SEQ ID NO 144
<211> LENGTH: 16
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 144

Glu Asn Gly Glu Pro Arg Gly Asp Asn Tyr Arg Ala Tyr Glu Asp Glu
  1               5                  10                  15

<210> SEQ ID NO 145
<211> LENGTH: 15
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 145

Glu Asn Gly Glu Pro Arg Gly Asp Asn Tyr Arg Ala Tyr Glu Asp
  1               5                  10                  15

<210> SEQ ID NO 146
<211> LENGTH: 14
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 146

Glu Asn Gly Glu Pro Arg Gly Asp Asn Tyr Arg Ala Tyr Glu
  1               5                  10

<210> SEQ ID NO 147
<211> LENGTH: 13
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 147

Glu Asn Gly Glu Pro Arg Gly Asp Asn Tyr Arg Ala Tyr
  1               5                  10

<210> SEQ ID NO 148
<211> LENGTH: 12
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.
```

```
<400> SEQUENCE: 148

Glu Asn Gly Glu Pro Arg Gly Asp Asn Tyr Arg Ala
 1               5                  10

<210> SEQ ID NO 149
<211> LENGTH: 11
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 149

Glu Asn Gly Glu Pro Arg Gly Asp Asn Tyr Arg
 1               5                  10

<210> SEQ ID NO 150
<211> LENGTH: 9
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 150

Glu Asn Gly Glu Pro Arg Gly Asp Asn
 1               5

<210> SEQ ID NO 151
<211> LENGTH: 8
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 151

Glu Asn Gly Glu Pro Arg Gly Asp
 1               5

<210> SEQ ID NO 152
<211> LENGTH: 21
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 152

Asn Gly Glu Pro Arg Gly Asp Asn Tyr Arg Ala Tyr Glu Asp Glu Tyr
 1               5                  10                  15

Ser Tyr Phe Lys Gly
            20

<210> SEQ ID NO 153
<211> LENGTH: 20
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.
```

<400> SEQUENCE: 153

Asn Gly Glu Pro Arg Gly Asp Asn Tyr Arg Ala Tyr Glu Asp Glu Tyr
1               5                   10                  15

Ser Tyr Phe Lys
            20

<210> SEQ ID NO 154
<211> LENGTH: 19
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 154

Asn Gly Glu Pro Arg Gly Asp Asn Tyr Arg Ala Tyr Glu Asp Glu Tyr
1               5                   10                  15

Ser Tyr Phe

<210> SEQ ID NO 155
<211> LENGTH: 18
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 155

Asn Gly Glu Pro Arg Gly Asp Asn Tyr Arg Ala Tyr Glu Asp Glu Tyr
1               5                   10                  15

Ser Tyr

<210> SEQ ID NO 156
<211> LENGTH: 17
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 156

Asn Gly Glu Pro Arg Gly Asp Asn Tyr Arg Ala Tyr Glu Asp Glu Tyr
1               5                   10                  15

Ser

<210> SEQ ID NO 157
<211> LENGTH: 16
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 157

Asn Gly Glu Pro Arg Gly Asp Asn Tyr Arg Ala Tyr Glu Asp Glu Tyr
1               5                   10                  15

<210> SEQ ID NO 158
<211> LENGTH: 15
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

```
<400> SEQUENCE: 158

Asn Gly Glu Pro Arg Gly Asp Asn Tyr Arg Ala Tyr Glu Asp Glu
 1               5                  10                  15

<210> SEQ ID NO 159
<211> LENGTH: 14
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 159

Asn Gly Glu Pro Arg Gly Asp Asn Tyr Arg Ala Tyr Glu Asp
 1               5                  10

<210> SEQ ID NO 160
<211> LENGTH: 13
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 160

Asn Gly Glu Pro Arg Gly Asp Asn Tyr Arg Ala Tyr Glu
 1               5                  10

<210> SEQ ID NO 161
<211> LENGTH: 12
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 161

Asn Gly Glu Pro Arg Gly Asp Asn Tyr Arg Ala Tyr
 1               5                  10

<210> SEQ ID NO 162
<211> LENGTH: 11
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 162

Asn Gly Glu Pro Arg Gly Asp Asn Tyr Arg Ala
 1               5                  10

<210> SEQ ID NO 163
<211> LENGTH: 10
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 163

Asn Gly Glu Pro Arg Gly Asp Asn Tyr Arg
 1               5                  10

<210> SEQ ID NO 164
<211> LENGTH: 9
<212> TYPE: PRT
```

```
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 164

Asn Gly Glu Pro Arg Gly Asp Asn Tyr
 1               5

<210> SEQ ID NO 165
<211> LENGTH: 8
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 165

Asn Gly Glu Pro Arg Gly Asp Asn
 1               5

<210> SEQ ID NO 166
<211> LENGTH: 7
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 166

Asn Gly Glu Pro Arg Gly Asp
 1               5

<210> SEQ ID NO 167
<211> LENGTH: 20
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 167

Gly Glu Pro Arg Gly Asp Asn Tyr Arg Ala Tyr Glu Asp Glu Tyr Ser
 1               5                  10                  15

Tyr Phe Lys Gly
             20

<210> SEQ ID NO 168
<211> LENGTH: 19
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 168

Gly Glu Pro Arg Gly Asp Asn Tyr Arg Ala Tyr Glu Asp Glu Tyr Ser
 1               5                  10                  15

Tyr Phe Lys

<210> SEQ ID NO 169
<211> LENGTH: 18
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.
```

-continued

<400> SEQUENCE: 169

Gly Glu Pro Arg Gly Asp Asn Tyr Arg Ala Tyr Glu Asp Glu Tyr Ser
1               5                   10                  15
Tyr Phe

<210> SEQ ID NO 170
<211> LENGTH: 17
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 170

Gly Glu Pro Arg Gly Asp Asn Tyr Arg Ala Tyr Glu Asp Glu Tyr Ser
1               5                   10                  15
Tyr

<210> SEQ ID NO 171
<211> LENGTH: 16
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 171

Gly Glu Pro Arg Gly Asp Asn Tyr Arg Ala Tyr Glu Asp Glu Tyr Ser
1               5                   10                  15

<210> SEQ ID NO 172
<211> LENGTH: 15
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 172

Gly Glu Pro Arg Gly Asp Asn Tyr Arg Ala Tyr Glu Asp Glu Tyr
1               5                   10                  15

<210> SEQ ID NO 173
<211> LENGTH: 14
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 173

Gly Glu Pro Arg Gly Asp Asn Tyr Arg Ala Tyr Glu Asp Glu
1               5                   10

<210> SEQ ID NO 174
<211> LENGTH: 13
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 174

Gly Glu Pro Arg Gly Asp Asn Tyr Arg Ala Tyr Glu Asp
1               5                   10

```
<210> SEQ ID NO 175
<211> LENGTH: 12
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 175

Gly Glu Pro Arg Gly Asp Asn Tyr Arg Ala Tyr Glu
 1               5                  10

<210> SEQ ID NO 176
<211> LENGTH: 11
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 176

Gly Glu Pro Arg Gly Asp Asn Tyr Arg Ala Tyr
 1               5                  10

<210> SEQ ID NO 177
<211> LENGTH: 10
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 177

Gly Glu Pro Arg Gly Asp Asn Tyr Arg Ala
 1               5                  10

<210> SEQ ID NO 178
<211> LENGTH: 9
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 178

Gly Glu Pro Arg Gly Asp Asn Tyr Arg
 1               5

<210> SEQ ID NO 179
<211> LENGTH: 8
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.

<400> SEQUENCE: 179

Gly Glu Pro Arg Gly Asp Asn Tyr
 1               5

<210> SEQ ID NO 180
<211> LENGTH: 7
<212> TYPE: PRT
<213> ORGANISM: Homo sapiens
<220> FEATURE:
<223> OTHER INFORMATION: Fragment peptide from bone sialoprotein (BSP).
<223> OTHER INFORMATION: The peptide has a C-terminal amide group.
```

-continued

```
<400> SEQUENCE: 180

Gly Glu Pro Arg Gly Asp Asn
 1               5
```